(12) United States Patent
Grunkin et al.

(10) Patent No.: US 8,731,845 B2
(45) Date of Patent: May 20, 2014

(54) METHOD AND A SYSTEM FOR DETERMINING A TARGET IN A BIOLOGICAL SAMPLE BY IMAGE ANALYSIS

(75) Inventors: Michael Grunkin, Skodsborg (DK); Niels Tækker Foged, Vekso (DK)

(73) Assignee: Visionpharm A/S, Horsholm (DK)

( * ) Notice: Subject to any disclaimer, the term of this patent is extended or adjusted under 35 U.S.C. 154(b) by 324 days.

(21) Appl. No.: 13/058,385

(22) PCT Filed: Aug. 14, 2009

(86) PCT No.: PCT/DK2009/050202
§ 371 (c)(1),
(2), (4) Date: Jun. 20, 2011

(87) PCT Pub. No.: WO2010/017822
PCT Pub. Date: Feb. 18, 2010

(65) Prior Publication Data
US 2011/0234812 A1      Sep. 29, 2011

(30) Foreign Application Priority Data
Aug. 15, 2008  (DK) .............................. 2008 01107

(51) Int. Cl.
*G01N 33/48* (2006.01)
*G06F 19/26* (2011.01)
*G06F 17/18* (2006.01)

(52) U.S. Cl.
CPC ............... *G06F 19/26* (2013.01); *G06F 17/18* (2013.01)
USPC ........................................................ 702/21

(58) Field of Classification Search
CPC ..................................................... G06F 19/26
USPC ....................................................... 702/21
See application file for complete search history.

(56) References Cited

U.S. PATENT DOCUMENTS

| | | | |
|---|---|---|---|
| 4,982,162 A | 1/1991 | Zakhor et al. | |
| 5,281,517 A | 1/1994 | Bacus et al. | |
| 5,548,661 A | 8/1996 | Price et al. | |
| 5,939,281 A | 8/1999 | Lehmann et al. | |
| 6,466,690 B2 | 10/2002 | Bacus et al. | |
| 6,962,789 B2 | 11/2005 | Bacus | |
| 7,079,675 B2 | 7/2006 | Hamer et al. | |
| 7,085,426 B2 | 8/2006 | August | |
| 7,130,484 B2 | 10/2006 | August | |
| 7,200,252 B2 | 4/2007 | Douglass | |
| 7,219,016 B2 | 5/2007 | Rimm et al. | |
| 7,266,249 B2 | 9/2007 | Ghosh et al. | |
| 2003/0185450 A1 | 10/2003 | Garakani et al. | |
| 2004/0029213 A1 | 2/2004 | Callahan et al. | |
| 2007/0047838 A1 | 3/2007 | Milanfar et al. | |
| 2008/0031521 A1 | 2/2008 | Can et al. | |

FOREIGN PATENT DOCUMENTS

| | | |
|---|---|---|
| WO | WO 01/51928 | 7/2001 |
| WO | WO 03/060653 | 7/2003 |
| WO | WO 2005/024651 | 3/2005 |
| WO | WO 2007/084363 | 6/2007 |
| WO | WO 2007/081088 | 7/2007 |
| WO | WO 2007/089777 | 8/2007 |
| WO | WO 2007/095644 | 8/2007 |
| WO | WO 2008/060403 | 7/2008 |

OTHER PUBLICATIONS

Brügmann et al., 2011, Digital Image analysis of membrane connectivity is a robust measure of HER2 Immunostains, Breast Cancer Res Treat, Springer Sciencei+Business Media.
Gustafsdottir et al., 2005, "Proximity ligation assays for sensitive and specific protein analyses", Anal Biochem. 345, 1, pp. 2-9.
Perko et al., 2004, "Efficient implementation of higher order image Interpolation", WSCG SHORT.
Ronneberger et al., "Spatial quantitative analysis of fluorescently labeled nuclear structures: Problems, methods, pitfalls", Chromosome Research, Kluwer Academic Publishers, DD, vol. 16, No. 3, May 8, 2008, pp. 523-562.
Sato, Y., "Hessian-based multiscale enhancement, description, and quantification of second-order 3-D local structures from medical volume data", In: "Handbook of medical image analysis, vol. II: Segmentation models part B", 2005, Kluwer Academic, pp. 531-589.
Takeda et al, 2007, "Kernel Regression for image processing and reconstruction", IEEE Transactions on Image Processing, vol. 16, No. 2, pp. 349-366.

(Continued)

*Primary Examiner* — Jerry Lin
(74) *Attorney, Agent, or Firm* — Gifford, Krass, Sprinkle, Anderson & Citkowski, P.C.

(57) ABSTRACT

The present invention relates to methods for identifying and optionally quantifying stained cells in a cell or tissue sample and determining expression level of a target, as well as methods for determining staining intensity and/or staining quality of a stained sample, calibrating digital imaging apparatus using the methods, as well as systems and a computer readable mediums therefore. In particular the invention relates to a method for identifying stained targets in a sample and uses of said method, said method comprising providing at least one digital representation of the sample wherein the sample has been stained with a stain staining a target, and filtering the digital representation with at least three filters, each of said filters comprising filter constants), applying said filter constant(s) to each pixels in at least a subset of the digital representation and determining an eigensolution based on the filter output for each pixel in the subset, wherein said filters are capable of enhancing the stained targets obtaining a filtered representation, segmenting the digital representation based on information from the optionally normalized filtered representation into stained cell targets and background, optionally combining with the digital representation, thereby obtaining a segmented representation, wherein said segmented representation discriminates between stained targets and other structures in the digital representation, and from said segmented representation identifying the stained targets in the sample.

37 Claims, 22 Drawing Sheets

(56) References Cited

OTHER PUBLICATIONS

Grunkin et al., "Practical Considerations of Image Analysis and Quantification of Signal Transduction IHC Staining," Signal Transduction Immunohistochemistry, Methods in Molecular Biology, vol. 717, part 3, pp. 143-154, 2011.

Laurinaviciene et al., "Membrane Connectivity Estimated by Digital Image Analysis of HER2 Immunohistochemistry is Concordant with Visual Scoring and Fluoroscence in situ Hybridization Results: Algorithm Evaluation on Breast Cancer Tissue Microarrays," Diagnostis Pathology, 6, 87, pp. 1-10, 2011.

Skaland, "Proliferation of Breast Cancer. Immunohistochemistry and Digital Image Analysis," Ph.D.—thesis at University of Bergen, Sep. 2009.

METHOD AND A SYSTEM FOR DETERMINING A TARGET IN A BIOLOGICAL SAMPLE BY IMAGE ANALYSIS

FIELD OF INVENTION

The present invention relates to methods for identifying and optionally quantifying stained cells in a cell or tissue sample, as well as a system and a computer readable medium therefore.

BACKGROUND OF INVENTION

In aiding a clinician in the diagnosis of cancer, a pathologist faces two key problems. First, the pathologist must determine whether a tissue or cell sample removed from a patient is benign or malignant. Second, upon reaching a determination that the tissue or cell sample is malignant, the pathologist must then classify the aggressiveness of the cancer and determine its clinical and biological behavior.

A diagnosis of cancer must be confirmed through histological examination of a tissue or cell sample removed from a patient. Such histological examination entails tissue-staining procedures that allow the morphological features of the tissue to be readily examined under a microscope. The pathologist, after having examined the stained tissue or cell sample, makes qualitative determinations of the state of the tissue or the patient from whom the sample was removed and whether the tumor is benign or malignant. The aggressiveness, invasiveness and ability to metastasize of the tumor, which alone or together determine the tumor malignancy are, however, difficult to ascertain using standard histological techniques.

Visual examination of tissue and cell samples is increasingly being augmented by the use of an automated (computer-aided) image analysis system. A representative system includes a computer that receives a magnified digital representation of the tissue or cell sample from a camera and processes the received digital representation. Image analysis is generally used to assess the affinity of stains for various biological markers. Examples of suitable affinity stains include chromogen- or fluorophor-based in situ detection of specific antibodies directed against the estrogen receptor (ER), the progesterone receptor (PR), the HER-2/neu protein, and the epidermal growth factor receptor (EGFR).

The coupling of affinity staining and computer-aided image analysis has permitted clinicians to better select optimal therapies for their patients e.g., hormone therapy for cancers that are ER and PR positive, and receptor antagonist therapy for cancers overexpressing a particular receptor, such as antibodies directed against HER-2/neu (Herceptin), or enzyme inhibitors directed against EGFR (Iressa, Tarceva).

However, a need exists for an automatic identification and quantification of specifically stained targets or markers for the classification of the tissue or cell sample being examined.

SUMMARY OF INVENTION

The present invention relates to a new image analysis method for use in diagnosis, prognosis and/or treatment prediction, wherein the new method is capable of enhancing and detecting stained markers manifesting themselves either as "blobs" in a tissue or cell, or arranged along particular linear tissue structures, or the cell membrane or nuclear membrane. The present method provides a tool for enhancing and detecting (identifying, segmenting) the stained parts in the representation of a tissue sample or cell sample, thereby facilitating subsequent processing of the representation and quantification of the staining.

Accordingly, in a first aspect the invention relates to a method for identifying stained targets in a sample, said method comprising
providing at least one digital representation of the sample wherein the sample has been stained with a stain staining a target, and
a) filtering the digital representation with at least three filters, each of said filters comprising filter constant(s), applying said filter constant(s) to each pixels in at least a subset of the digital representation and determining an eigensolution based on the filter output for each pixel in the subset, wherein said filters are capable of enhancing the stained targets obtaining a filtered representation,
b) optionally normalizing the filtered representation,
c) segmenting the digital representation based on information from the optionally normalized filtered representation into stained targets and background, optionally combining with the digital representation, thereby obtaining a segmented representation, wherein said segmented representation discriminates between stained targets and other structures in the digital representation, and
d) from said segmented representation identifying the stained cell targets in the biological cell sample.

In another aspect the invention relates to the use of the filtering method in a method for quantifying the stained target(s), said method comprising
providing at least one digital representation of the sample wherein the sample has been stained with a stain staining a target,
performing steps a)-c) as defined above obtaining a segmented representation,
from said segmented representation identifying the stained targets in the sample, and quantifying the staining target(s) in the digital representation.

In a third aspect the invention relates to a method for determining the staining intensity of stained targets, said method comprising
providing at least one digital representation of the sample wherein the sample has been stained with a stain staining a target
performing steps a)-c) as defined in above obtaining a segmented representation,
from said segmented representation identifying the stained targets in the sample, and calculating the staining intensity in the digital representation.

The methods of the invention may also be used for determining the expression level of a target in a cell sample, and accordingly, in a fourth aspect the invention relates to a method for determining an expression level of a target in a biological sample, said method comprising
providing at least one digital representation of the biological sample wherein the cell sample has been stained with a stain staining a target,
performing steps a)-c) as defined above obtaining a segmented representation,
from said segmented representation identifying the stained targets in the biological sample, and calculating the staining intensity in the segmented representation, thereby determining the expression level of the target.

The present invention may also be used in methods for calibrating the equipment used in the imaging processes. Accordingly, in a fifth aspect the invention relates to a method for providing a calibration curve of staining intensity for stained samples, said method comprising providing a plurality of digital representations of known samples wherein each sample has been stained with a known amount of stain, wherein the sample has been stained with a stain staining a target, performing steps a)-c) as defined above obtaining a segmented representation, from said segmented representation identifying the stained targets in the sample, and calculating the staining intensity in the segmented representation for each digital representation, thereby obtaining a calibration curve for the staining intensity.

And also, in a sixth aspect to a method for calibrating a digital imaging apparatus, comprising providing a plurality of digital representations of known samples wherein each sample has been stained with a known amount of stain, wherein the sample has been stained with a stain staining a target, performing steps a)-c) as defined above obtaining a segmented representation, from said segmented representation identifying the stained targets in the , and calculating the staining intensity in the segmented representation for each digital representation, comparing the calculated staining intensity with a calibration curve as defined above, thereby obtaining a calibration measure, and calibrating the digital imaging apparatus based on said calibration measure.

In order to obtain valid results from any staining method the staining quality of the stained targets are important, such as for example the dilution of the stains as well as the time spent for processing the stain. The present invention relates in a seventh aspect to a method for evaluating the staining quality of stained targets, said method comprising providing at least one digital representation of the sample wherein the sample has been stained with a stain staining a target, performing steps a)-c) as defined above obtaining a segmented representation, calculating the staining intensity in the segmented representation for each digital representation, comparing the calculated staining intensity with a calibration curve as defined above, and evaluating the staining quality of the stained targets.

The invention further relates to a method for classifying a sample, said method comprising identifying stained targets in said sample by a method as defined above, based on the identified stained targets classifying the sample in relation to two or more groups of samples.

The invention relates in further aspects to a computer readable medium comprising instructions for carrying out the methods as defined above.

Furthermore, the present invention relates to an automated system suitable for carrying out the method described above, comprising, in combination:

a database capable of including a plurality of digital representations of a plurality of biological specimens;

a software module for analyzing a plurality of pixels from a digital representation of a biological specimen; and a control module comprising instructions for carrying out any of the method defined above.

DETAILED DESCRIPTION OF THE INVENTION

Definitions

Figure 1A:
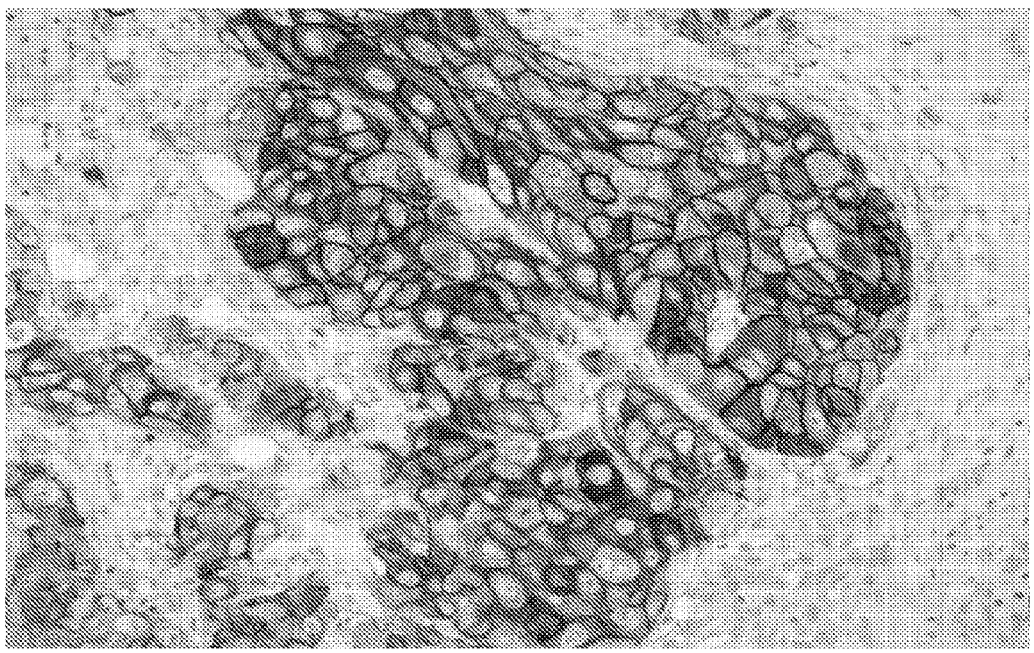
FIGS. 1a-d show a digital representation of a stained tissue sample (a) as well as three different results of filtering the digital representation using either the filter according to the invention (b) or Laplacian (c) or gradient (d).

Biological sample derived from a biological organism, such as a tissue sample or a body liquid sample. In most embodiments the biological sample is a biological cell sample.

Marker is used in its normal meaning, i.e. the part of the sample that may be used to identify whether the sample represents a particular condition, normally a disease or a disorder. Markers may be located in or on cells in the sample, or may be located extracellularly, such as targets lining specific structures in the sample. The term marker is used interchangeably with the term target.

Sample is any type of sample, preferably the sample is a biological sample.

Staining is used in its normal meaning, i.e. an aid to visualize the targets. The staining stains the targets, either directly or indirectly, but preferably does not stain any other parts of the sample, thereby enhancing the visibility of the targets.

Target is used in its normal meaning, i.e. the part of the sample that may be used to identify whether the sample represents a particular condition, normally a disease or a disorder. As described below targets may be located in or on cells in the sample, or may be located extracellularly, such as targets lining specific structures in the sample. The term target is used interchangeably with the term marker.

Classify or classification is used in its normal meaning, ie. determining whether a specific sample belongs to one of two or more classes or groups. An example of classification is shown in the Examples wherein the severity of a breast cancer sample is found by classifying the sample in one of the four classes: 0, 1+, 2+, 3+. In one embodiment the classification is based on determination of intensity and/or connectivity as discussed herein.

A cancer diagnosis, both an initial diagnosis of disease and subsequent monitoring of the disease course (before, during, or after treatment) is conventionally confirmed through histological examination of cell or tissue samples removed from a patient. Clinical pathologists need to be able to accurately determine whether the sample representing the tumor is benign or malignant and to classify the aggressiveness of tumor if deemed to be malignant, because these determinations often form the basis for selecting a suitable course of patient treatment. Similarly, the pathologist needs to be able to detect the extent to which a cancer has grown or gone into remission, particularly as a result of or consequent to treatment, most particularly treatment with chemotherapeutic or biological agents.

Histological examination traditionally entails tissue-staining procedures that permit morphological features of a sample to be readily observed under a microscope. A pathologist, after examining the stained sample, typically makes a qualitative or semi-quantitative determination of whether the tumor sample is malignant. Sometimes also a quantification is performed, this is however conducted manually. It is difficult, however, to ascertain a tumor's aggressive potential merely through histological examination of the sample, because a tumor's aggressive potential is often a result of the biochemistry of the cells within the tumor, such as protein expression or suppression and protein phosphorylation, which may or may not be reflected by the morphology of the sample. Therefore, it is important to be able to assess the biochemistry of the cells within a tumor sample. Cancer therapy can be based on molecular profiling of tumors rather than simply their histology or site of the disease.

Thus, not only the mere identification of stained targets but also the quantification of stained targets in a sample is relevant for providing a diagnosis, such as a cancer diagnosis.

The present invention provides methods for identifying, enhancing, and quantifying stained targets based on inventive filtering methods. The filtering methods are applied to digital representations of cell samples stained with a staining selective for the target to be visualised. Stained targets may be classified as blobs or lines.

Blobs means that the target appear in areas (often rounded) in the cells or outside the cells. Blobs may also be called spots. Blobs may represent anything from a single molecule to a group of molecules or even entire structures, such as nucleoli, nuclei or cells. Examples of targets presenting themselves as blobs are single or grouped proteins or peptides, such as lysozymes or a single receptor or groups of receptors.

Lines mean that the targets are arranged so that they appear as lines in the digital representation. Examples of targets appearing as lines are proteins or peptides, such as receptors, attached to the cell membrane essentially along the whole cell membrane. Lines may also be targets aligned along a structure or an organ in a tissue.

In the present context the term "representation" is used to describe a representation of the region to be examined, i.e. the term representation includes 1-dimensional representations, 2-dimensional representations, 3-dimensionals representations as well as n-dimensional representatives. Thus, the term representation includes a representation of the region, a volume of the region, a matrix of the region as well as an array of information of the region.

In the present context the term "background" is used to describe any other structure in the representation not representing the targets to be identified.

The present inventors have identified new filters suitable for enhancing blob-shaped and linear structures, respectively. The filtering method comprises applying filter constant(s) to the pixels in at least a subset of the digital representation of the sample. As described below, the filter constants may be determined so as to provide the polynomial coefficients of a spatial polynomial determined within a local window within the digital representation as a least squares fit to the intensity values within the said window. Preferably the polynomial is a second order polynomial, a fourth order polynomial, or a sixth order polynomial. Increasing orders of the polynomial will make the filters still more responsive to high-frequency content in the representation, and thereby also to noise. On the other hand, the local representation properties are also modeled far better by a higher-order polynomial. The choice of the polynomial order is therefore a trade-off, and may be chosen according to the specific application.

The number of filters may be selected depending on the specific application, however for most purposes it is preferred that at least three filter constants are applied to the pixels in the subset. The number of filter constants depends entirely upon the size of the window—i.e. the filter support.

The window size for the polynomial is preferably fitted to be greater than the size of the subset at the specific magnification used for obtaining the digital representation, and may be fitted for each representation, or more preferably a general fitted window size may be used for all representations in a series of representations having corresponding subset size, also called a universal window size.

The subset may correspond to any suitable portion of the digital representation, and the entire digital representation may be filtered in one embodiment.

When applying each of the filters in a sliding window across the digital representation or a subset of the digital representation, filtering process continues by determining an Eigensolution for each window location, thereby obtaining a filtered representation. By the term Eigensolution is understood Eigenvalue and/or Eigenvector.

In a preferred embodiment the Eigensolution is determined from a Hessian matrix wherein said Hessian matrix is generated from the Polynomial filters, as discussed below in greater detail. In particular the present inventor has found that the first Eigenvalue is suitable for enhancing locally linear structures, and the second Eigenvalue is suitable for enhancing blob-shaped structures.

Combining the filtered representation, optionally with the original spectral representation, the representation is then segmented into stained targets and background in order to obtain a segmented representation. The segmentation may be a simple thresholding process whereby the segmented representation shows the enhanced stained targets and has eliminated or substantially eliminated the background. In other embodiments, the segmentation may comprise a multi-variate Bayes classifier, or a multivariate (fuzzy) K-means clustering. Based on the segmented representation the stained targets may be further analysed, such as by quantifying characteristics associated with the stained targets.

The filtered representation may be normalized, such as normalized with the intensity representation, before any segmentation is initiated.

During the segmentation process the filtered representation may be combined with the digital representation in order to supply information from the digital representation to the segmented representation. This is particularly relevant when the digital representation contains information regarding for example colour of the staining.

The segmented representation may be post-processed before identifying the stained targets. In one embodiment the post-processing relates to elimination of stained cell membranes or stained cell blobs having an area below a predefined area whereby only the stained targets likely to be the relevant stained targets are identified.

In one embodiment the filter constants are estimated as described in the following.

The digital representation g(x,y) has been sampled with sampling densities $\Delta_x$ and $\Delta_y$ respectively. The sampled signal is then approximated with a smooth function in a window that, for the sake of simplicity, is assumed to be square. For the particular application considered here, however, the special case of a P'th order spatial polynomial defined as below is considered:

$$f(x, y) = \sum_{k=0}^{P} \sum_{l=0}^{P-k} \theta_{k,l} x^k y^l = \underline{\Theta}^T \underline{Z}(x, y)^T \quad (0.1)$$

Where the vector notation is employed:

$$\underline{\Theta}^T = [\theta_{k,l}, k=0, \ldots, P\, l=0, \ldots, P-k] \quad (0.2)$$

and $$\underline{Z}(x,y)^T = [x^k y^l, k=0, \ldots, P\, l=0, \ldots, P-k] \quad (0.3)$$

The coefficients of the polynomial may be determined using any suitable estimator, such as a Least-Squares estimator or a weighted Least-Squares estimator. The structure of a Least-Squares estimator is found as:

$$\hat{\underline{\Theta}} = \left( \sum_{i=-K}^{k} \sum_{j=-K}^{K} \underline{Z}(i \cdot \Delta_x, j \cdot \Delta_y) \underline{Z}(i \cdot \Delta_x, j \cdot \Delta_y)^T \right)^{-1} \quad (0.4)$$

$$\left( \sum_{i=-K}^{K} g(i \cdot \Delta_x, j \cdot \Delta_y) \underline{Z}(i \cdot \Delta_x, j \cdot \Delta_y) \right)$$

And the inverse coefficient matrix is:

$$\underline{B} = \left( \sum_{i=-K}^{k} \underline{Z}(i \cdot \Delta_x, j \cdot \Delta_y) \underline{Z}(i \cdot \Delta_x, j \cdot \Delta_y)^T \right)^{-1} \quad (0.5)$$

$$= \begin{pmatrix} b_{00} & b_{01} & \ldots & b_{0P} \\ b_{10} & b_{11} & \ldots & b_{1P} \\ \vdots & \vdots & \ddots & \vdots \\ b_{P1} & b_{P2} & \ldots & b_{PP} \end{pmatrix}$$

The coefficients can also be interpreted as a filter or convolution mask (used synonymously in the literature) with support on $[-K;K]\times[-K;K]$, where the filter has the form given below $$\Phi = \begin{pmatrix} \phi_{-K,-K} & \phi_{-K,-K+1} & \ldots & \phi_{-K,K} \\ \phi_{-K+1,-K} & \phi_{-K+1,-K+1} & \ldots & \phi_{-K+1,K} \\ \vdots & \vdots & \ddots & \vdots \\ \phi_{K,-K} & \phi_{K,-K+1} & \ldots & \phi_{K,K} \end{pmatrix} \quad (0.6)$$

And the filtered value is computed as $$G_\Phi(x, y) = \Phi \otimes g(x, y) = \sum_{i=-K}^{K} \sum_{j=-K}^{K} g(x + i \cdot \Delta_x, y + j \cdot \Delta_y) \cdot \phi_{i,j} \quad (0.7)$$

Each coefficient in the approximating polynomial can be interpreted as a filter or convolution mask. The individual filter weights may be computed as $$\Theta_{m,n}(k, l) = \left(\frac{1}{\Delta_x}\right)^m \left(\frac{1}{\Delta_y}\right)^n \sum_{i=0}^{P} \sum_{j=0}^{P-i} \underline{B}_{\frac{(2P+3-m)m+2n}{2},\frac{(2P+3-i)i+2j}{2}}(k)^i (l)^j = \quad (0.8)$$

$$\left(\frac{1}{\Delta_x}\right)^m \left(\frac{1}{\Delta_y}\right)^n \underline{B}_{\frac{(2P+3-m)m+2n}{2}, i} Z(k, l)$$

Where the indices are running over $m=0, \ldots, P\, k=-K, \ldots, K$ $n=0, \ldots, P-m, l=-K \ldots, K \quad (0.9)$ The value of a given coefficient, ie. a filter constant, is now computed as $$\theta_{ij}(x, y) = \Theta_{ij} \otimes g(x, y) = \sum_{k=-K}^{K} \sum_{l=-K}^{K} \Theta_{ij}(k, l) \cdot g(x - k, y - l) \quad (0.10)$$

For most practical applications it is suitable to use a second-order polynomial, as discussed in the following:

A spatial second-order polynomial defined on $(x,y)\epsilon[-K;K]\times[-K;K]$ with $\Delta_x=\Delta_y=1$, is defined as (Equation 0.1):

$f(x,y)=\theta_{00}+\theta_{01}y+\theta_{02}y^2+\theta_{10}x+\theta_{11}xy+\theta_{20}x^2=\underline{\Theta}^T\underline{Z}(x,y)$ with $\underline{\Theta}^T=[\theta_{00},\theta_{01},\theta_{02},\theta_{10},\theta_{11}\theta_{02}]$ and $\underline{Z}(x,y)^T=[1,y,y^2,x,xy,x^2]$ The coefficient matrix is calculated as described in Equation 0.5, as shown below:

$$\sum_{x=-K}^{K} \sum_{y=-K}^{K} \underline{Z}(x, y)\underline{Z}(x, y)^T = \sum_{x=-K}^{K} \sum_{y=-K}^{K} \begin{pmatrix} 1 & y & y^2 & x & xy & x^2 \\ y & y^2 & y^3 & xy & xy^2 & x^2 y \\ y^2 & y^3 & y^4 & xy^2 & xy^3 & x^2 y^2 \\ x & xy & xy^2 & x^2 & x^2 y & x^3 \\ xy & x^2 y & x^3 y & x^2 y & x^2 y^2 & x^3 y \\ x^2 & x^2 y & x^2 y^2 & x^3 & x^3 y & x^4 \end{pmatrix} =$$

$$\frac{1}{3}(2K+1)^2(K+1)K$$

-continued $$\begin{pmatrix} \frac{3}{K(K+1)} & 0 & 1 & 0 & 0 & 1 \\ 0 & 1 & 0 & 0 & 0 & 0 \\ 1 & 0 & \frac{1}{5}(3K^2+3K-1) & 0 & 0 & \frac{1}{3}K(K+1) \\ 0 & 0 & 0 & 1 & 0 & 0 \\ 0 & 0 & 0 & 0 & \frac{1}{3}K(K+1) & 0 \\ 1 & 0 & \frac{1}{3}K(K+1) & 0 & 0 & \frac{1}{5}(3K^2+3K-1) \end{pmatrix}$$

The inverse coefficient matrix is obtained as:

$$\underline{B} = \frac{3}{(2K+1)^2(2K+3)(2K-1)}.$$

$$\begin{pmatrix} \frac{1}{3}\begin{pmatrix}14K^2+\\14K-3\end{pmatrix} & 0 & -5 & 0 & 0 & -5 \\ 0 & \frac{(2K+3)(2K-1)}{K(K+1)} & 0 & 0 & 0 & 0 \\ -5 & 0 & \frac{15}{K(K+1)} & 0 & 0 & 0 \\ 0 & 0 & 0 & \frac{(2K+3)(2K-1)}{K(K+1)} & 0 & 0 \\ 0 & 0 & 0 & 0 & \frac{3(2K+3)(2K-1)}{(K+1)^2K^2} & 0 \\ -5 & 0 & 0 & 0 & 0 & \frac{15}{K(K+1)} \end{pmatrix}$$

Using this expression and Equation 0.8, the convolution masks corresponding to each of the coefficients in the polynomial are readily obtained.

$$\Theta_{00}(k,l) = \underline{B}_{0\square} Z(k,l) =$$
$$\frac{1}{(2K+1)^2(2K+1)(2K-1)}((14K^2+14K-3)-15l^2-15k^2)$$

$$\Theta_{01}(k,l) = \underline{B}_{1\square} Z(k,l) \frac{3}{(2K+1)^2 K(K+1)} l$$

$$\Theta_{02}(k,l) = \underline{B}_{2\square} Z(k,l) = \frac{15}{(2K+1)^2(2K+3)(2K-1)}\left(-1+\frac{3l^2}{K(K+1)}\right)$$

$$\Theta_{10}(k,l) = \underline{B}_{1\square} Z(k,l) = \frac{3}{(2K+1)^2 K(K+1)} k$$

$$\Theta_{11}(k,l) = \underline{B}_{1\square} Z(k,l) = \frac{9}{(2K+1)^2 K^2(K+1)^2} k \cdot l$$

$$\Theta_{20}(k,l) = \underline{B}_{2\square} Z(k,l) = \frac{15}{(2K+1)^2(2K+3)(2K-1)}\left(-1+\frac{3k^2}{K(K+1)}\right)$$

This local representation approximation may be used for extracting information about the local representation properties. The i,j'th order derivative is obtained using $$\frac{\partial^{ij}}{\partial^i x \partial^j y} f(x,y) = w(i) \cdot w(j) \theta_{ij}(x,y) \quad (0.11)$$

-continued $$w(i) = \begin{cases} 1, & i > 0 \\ i, & i = 0 \end{cases}$$

In a preferred embodiment, after having applied the estimated filter constants to the representation, then the Hessian matrix may be established:

$$\underline{H}(x,y) = \begin{pmatrix} \theta_{20}(x,y) & \theta_{11}(x,y) \\ \theta_{11}(x,y) & \theta_{02}(x,y) \end{pmatrix} \quad (0.12)$$

And based on the Hessian matrix, the Eigen values may be computed as $$\begin{pmatrix} \lambda_1(x,y) \\ \lambda_2(x,y) \end{pmatrix} = \quad (0.13)$$
$$\frac{1}{2}\begin{pmatrix} \theta_{20}(x,y)+\theta_{02}(x,y)+\sqrt{(\theta_{20}(x,y)-\theta_{02}(x,y))^2+4\theta_{11}(x,y)^2} \\ \theta_{20}(x,y)+\theta_{02}(x,y)-\sqrt{(\theta_{20}(x,y)-\theta_{02}(x,y))^2+4\theta_{11}(x,y)^2} \end{pmatrix}$$

It is noted that $\lambda_1(x,y)+\lambda_2(x,y)=\theta_{20}(x,y)+\theta_{02}(x,y)$ may be recognized as the Laplacian. These new filters represent a non-linear combination of the directional derivatives. A simple interpretation of the first eigenvalue is that it is related to the maximum local curvature (more accurately the generalized variance), whereas the second eigenvalue is the curvature in a direction perpendicular to the first eigenvalue.

Accordingly, the first eigen filter enhances linear structures, such as cell membranes, whereas the second eigen filter has a tendency towards enhancing blob-shaped structures, such as grouped stained markers.

FIGS. 1a-1d shows the advantages of using the filters of the present invention for enhancing stained targets associated with cell membranes, as compared to filters using Laplacian and a gradient.

Figure 1B:
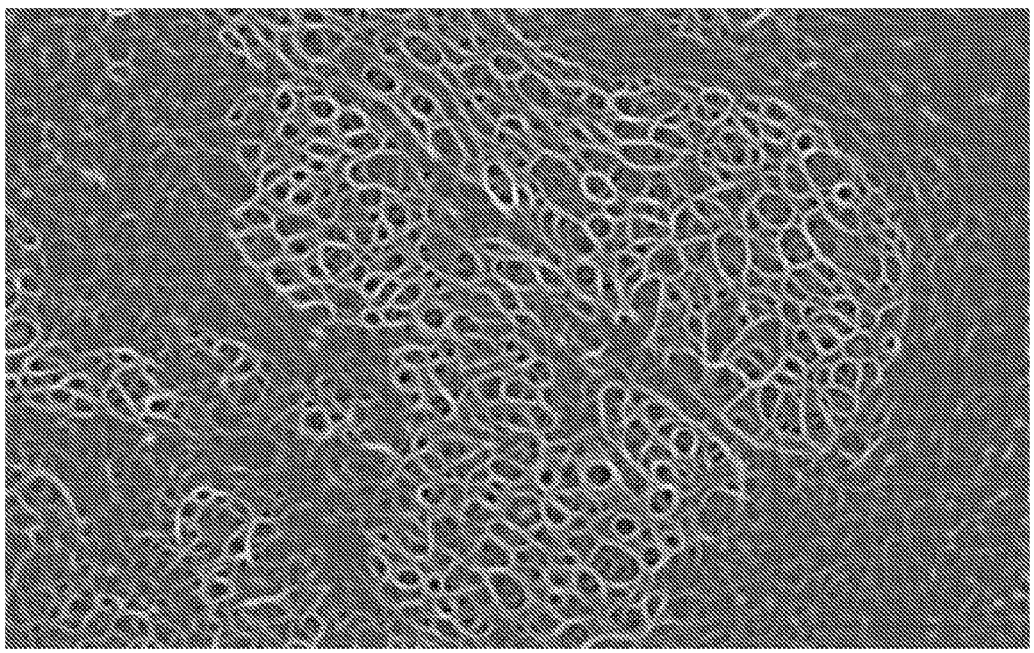

FIG. 1a shows the representation of a tissue sample, wherein a target associated with the cell membrane is stained. FIG. 1b shows the filtered representation, wherein a filter according to the invention relevant for cell membranes is used, ie. a filter using the first Eigenvalue of a Hessian matrix from a second order derivative. The stained cell membranes are clearly enhanced from the background.

Figure 1C:
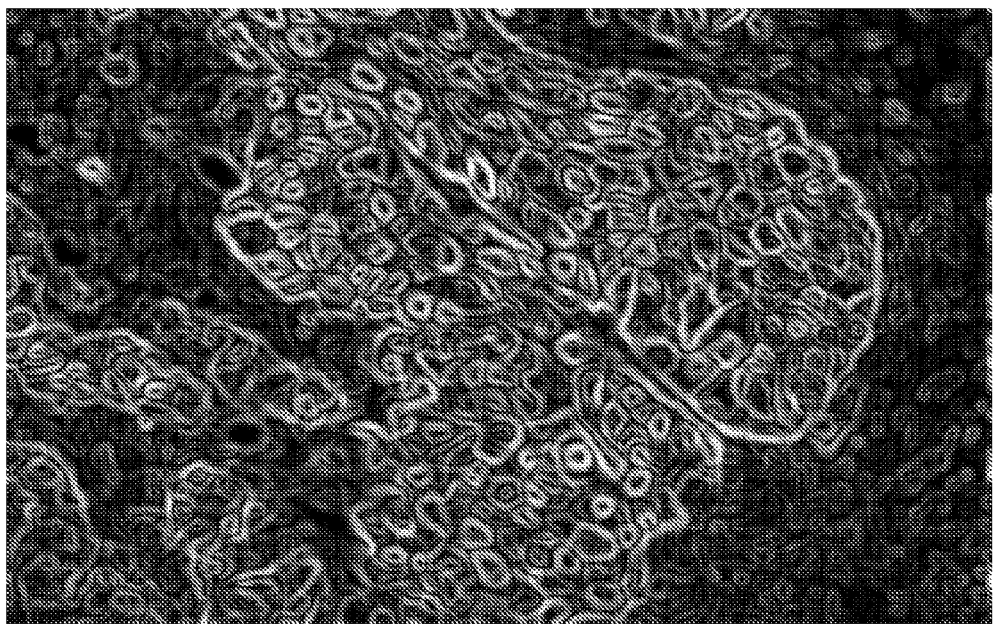
Figure 1D:
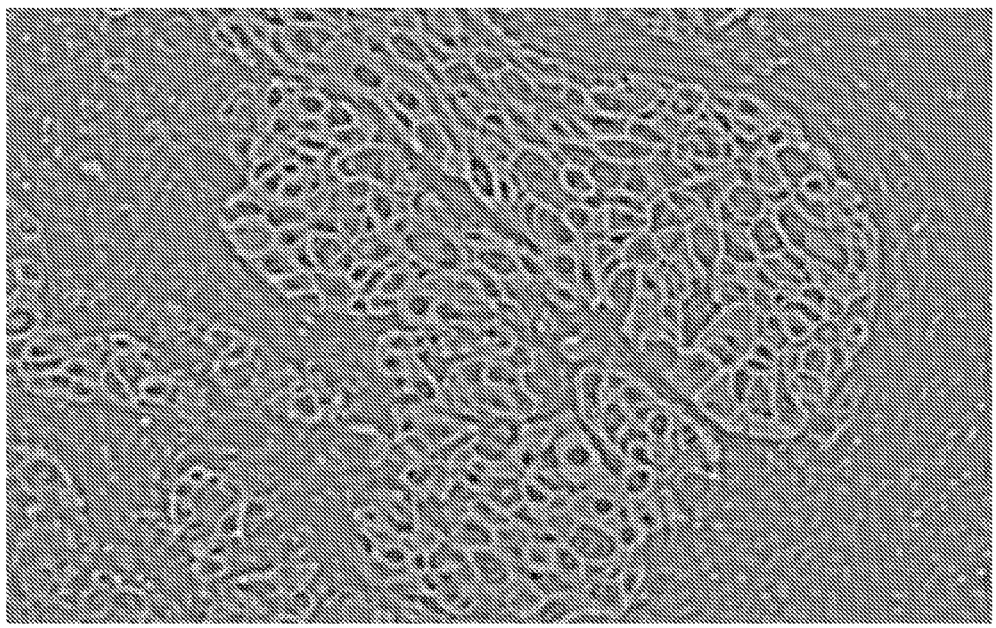

FIGS. 1c and 1d show the result of filtering with another filter, wherein FIG. 1c filters using a gradient (first order derivative)—note the "double lines" in relation to the cell membranes. In FIG. 1d a Laplacian filter is used, and it is clear from the figure that the result is a blurred representation as compared to the cell membranes in FIG. 1b.

FIGS. 2a-d show an embodiment of the present invention. FIG. 2a shows a digital representation of a cell sample. FIG. 2b shows a filtered representation, being filtered with a method according to the invention using a second-order polynomial. FIG. 2c shows a segmented represention, and FIG. 2d shows the segmented representation after post-processing whereby stain areas having a size too small for being relevant cell membranes are removed. The stained targets may be identified from the segmented, post-processed representation of FIG. 2d and may furthermore be quantified.

Figure 2:
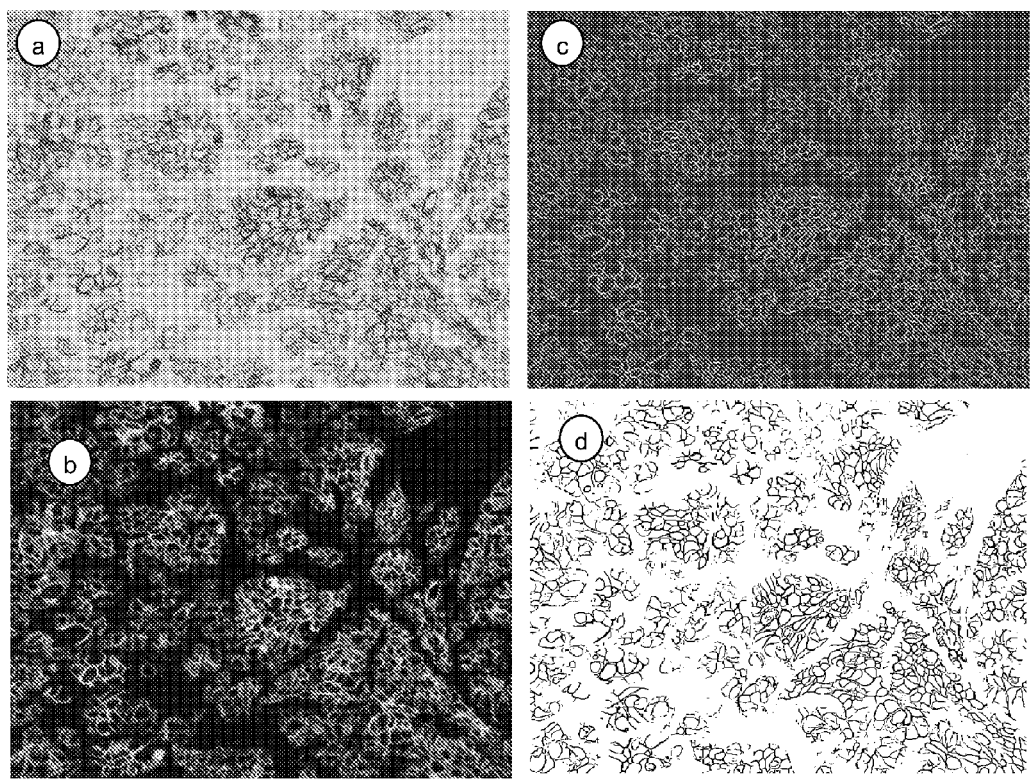
FIGS. 2a-d show the method of the invention from digital representation to segmented representation.

As shown in FIGS. 1 and 2 the present invention provides a method for enhancing stained targets, thereby facilitating identification of stained targets.

Apart from mere identification of stained targets in the digital representation the present invention is also useful for quantification of the stained targets in the digital representation, thereby providing the opportunity of classifying or grading the various cell or tissue samples based in the amount of stained target. For example in cancer diagnostics the amount of stained target may provide an important diagnostic tool informing of the severity of the disease. An example hereof is in the breast cancer diagnostics, wherein the quantification of stained Her-2 leads to a grading of the cell sample, and based on such a grading the physician is capable of determining the relevant treatment with a higher chance of success. For many purposes one type of targets are stained, such as one specific receptor. However, in some embodiments it is found advantageous to stain two different targets, such as two different receptors, normally by two different stains, each stain exclusively staining one target only. Thereby the methods according to the invention may identify the two different stained targets, normally in two different identification procedures, and subsequently quantification, classification etc may be conducted on the basis of the total information of the two targets.

The amount of stained target may be quantified by measuring the intensity of stained targets, such as the average staining intensity. The amount of stained target may also be determined by determining the diameter of each blob or the area of each blob, as well as determining the length of each line or the area of each line. The length of a cell membrane may for example be quantified by counting neighbouring pixels (measuring the skeleton of the cell membrane) not taking into account the thickness of the membrane.

In one embodiment chromaticity is used as a measure of the staining intensity. When studying cell membranes being stained it has been found that the red or blue chromaticity value is especially useful, more preferably red chromaticity value.

In another embodiment, the normalized so-called brown feature (defined below) is used as a measure of staining intensity.

The brown feature may be computed using simple manipulation of color contrasts as described below:

$F1$=Abs(Red−Blue)(The absolute value of the Red intensity minus the Blue intensity calculated pixel by pixel)

Normalized Brown=(255−(Blue+$F1$))/255

A different measure expressing staining intensity may be computed as follows: The staining intensity is divided into groups, such as three groups representing the strong intensity, the medium intensity as well as the weak intensity. By computing the area under curve for each group, getting for example $$A_{total}=A_{strong}+A_{medium}+A_{weak}$$

Different cut-offs in intensity may be defined for these.

Then relative values, such as $A_{strong}/A_{total}$ may be used as an alternative staining intensity measure.

It may also be possible to use Atotal=Astrong+Aother, where different cut-offs (thresholds) may be used to discriminate between Strong and Other depending on reagents, imaging, and other. As above, relative measures may be used.

The advantage of the approach outlined above is that it has the potential to decrease the need for having different diagnostic decision thresholds for different reagents (e.g. Dako, Ventana, Novocastra) when intensity measures are employed for diagnostic decision making.

In particularly when studying objects being defined by a line, such as cells being defined by the cell membrane, it may be advantageous to supplement with a measure for connectivity. Connectivity is used as a measure for defined objects wherein the lines defining the objects appears continuous in the image, such as for example when the cell membrane is stained in its whole circumference without any defects.

Connectivity may be measured as the area of lines continuously defining the objects divided by the number of connected cell membranes in the image: In other words the average size of connected positive stained membrane objects detected in the image see also Example 3 showing an embodiment of this. In particularly in cancer diagnostics wherein the amount of stained receptors or proteins on a cell membrane may be taken as a measure of severity of the disease, connectivity may add important information to the diagnostic.

In one embodiment the quantification is used for determining the expression level of a target in a biological cell sample, whereby the expression level is determined by either staining the mRNA or staining the resulting polypeptide and quantifying the stained targets, for example by determining the staining intensity. The staining intensity may thereby be a measure for the expression level of the target.

In another embodiment the methods according to the invention may be used to determine the presence of homodimers or heterodimers of receptors. In the tumor diagnostic HER2 is often used, and HER2 is in the family of VEGFR, namely HER1, HER2, HER3, HER4, each of which may form homodimers and heterodimers. In order to determine whether homodimers or heterodimers are formed, each receptor is stained with a different colour. It is then possible by the methods of the invention to determine the stained receptors and subsequently determine the colour of each staining, thereby determining whether the two receptors in the dimer are identical or different due to the colouring of the blobs representing the receptors.

Also there are recent methods, which only allow a staining to take place if two different targets are sufficiently close to each other. The Proximity Ligation Assay (PLA) (Proximity ligation assays for sensitive and specific protein analyses. Gustafsdottir S M, Schallmeiner E, Fredriksson S, Gullberg M, Söderberg O, Jarvius M, Jarvius J, Howell M, Landegren U. Anal Biochem. 2005 345(1):2-9) for example can be made selective for heterodimers of HER-receptors if including two antibodies recognizing proximal epitopes on two different HER monomers. Only if the antibodies are bound simultaneously to their respective target, and are sufficiently close typically due to the heterodimerization of their targets, a staining reaction will be possible. In another embodiment the methods according to the present invention will, when applied to tissue samples stained by PLA or similar histochemical techniques, be of importance for the specific identification and quantification of only biologically active targets such as receptor heterodimers, phosphorylated receptors, ligand-binding receptors, and transcription factors bound to their corresponding DNA sequences.

In another embodiment the methods according to the invention allow for detection of amplification or deletion of a gene. This may be accomplished by staining a marker for the target gene and staining a marker for a reference gene typically but not necessarily located on the same chromosome as the target gene. Every gene copy will be represented by a specifically stained blob. If the ratio of target gene blobs to reference gene blobs is substantially higher than 1 it strongly indicates an amplification of that target gene. If the ratio of target gene blobs to reference gene blobs is substantially lower than 1 it strongly indicates a deletion of that target gene. Such detection of amplification or deletion may for example be relevant in the diagnosis of solid tumors, such as breast cancer, where for example HER-2 gene amplification has prognostic as well as Herceptin predictive consequences.

In yet another embodiment the methods according to the invention allow for detection of translocation of a gene. This may be accomplished by staining a marker for the gene and staining a marker being located next to the gene in the normal population. If the two markers are close, ie. seen as two markers next to each other then no translocation has happened, whereas if the two markers are found spaced apart from each other then it is likely that a translocation has happened. Such detection of translocation may for example be relevant in the diagnosis of lymphoma. The two markers may have the same staining or differently-coloured staining.

The present invention may also be used for determining co-localisation, ie. whether two stained markers are present in the same cell nucleus or in the cell nuclei of two neighbouring cells. This may for example be determined by determining the distance between the two stained markers.

The present invention may be applied to any cell sample. By the term "cell sample" is meant biological samples comprising cells, most preferably tumor cells, that are isolated from body samples, such as, but not limited to, smears, sputum, biopsies, secretions, cerebrospinal fluid, bile, blood, lymph fluid, urine and feces, or tissue which has been removed from organs, such as breast, lung, intestine, skin, cervix, prostate, and stomach. For example, a tissue sample can comprise a region of functionally related cells or adjacent cells. In one preferred embodiment, the specimen includes a plurality of cells, such as human cells, such as a plurality of human cells potentially including one or more human cancer cells, such as breast cancer cells.

In order to aid identify cells being relevant for the condition or disease being examined a staining specific for target(s) indicative for said condition or disease is applied to the sample before the digital representation is acquired.

The targets may be polypeptides, such as receptors, associated with the condition or disease capable of being visualised and optionally quantified by image analysis using a suitable and specific binding between the target and a molecule carrying the staining substance.

Examples of targets typically associated with the cell membrane are: the HER-family, ie. HER1, HER2, HER3, and HER4; cytokeratines; CD-antigens.

Examples of targets typically within the cell nucleus are: Estrogen receptor (ER), progesterone receptor (PR), androgen receptor (AR), Ki-67, and p53 as well as a high number of different gene targets involved in chromosomal aberrations (eg. Topoisomerase II alpha (TOP2A)).

Examples of targets typically found within the cytoplasm are: AKT, Mitogen-Activated Protein Kinase ("MAP kinase" or MAPK), PI-3 kinase, catenins, and MMPs.

Examples of targets typically also found extracellularly are: VEGFR, and TIMP-1.

Specific examples of targets include but are not limited to tumor antigens such as CA15-3 (breast cancer), CA19-9 (gastrointestinal and pancreatic cancer), CA125 (ovarian cancer), CA242 (gastrointestinal cancer), p53 (colorectal cancer), prostate-specific acid phosphatase (prostate cancer), prostate-specific antigen (PSA) (prostate cancer), Rb (retinoblastoma), CD56 (small cell lung cancer), prostate-specific antigen (prostate cancer), carcinoembryonic antigen (CEA) (colon cancer), melanoma antigen and melanoma-associated antigens (melanoma), mucin-1 (carcinoma), HER2 (breast cancer), HER2/neu (breast cancer) EGFR (breast and ovarian cancer), CA27-29 (breast cancer), nuclear matrix protein 22 (NMP22) (bladder cancer), bladder tumor-associated antigen (BTA) (bladder cancer), KIT (gastroinstestinal cancer), α-fetoprotein (αFP) (nonseminoma testicular cancer), β-human chorionic gonadotropin (βHCG) (testicular cancer), thyroglobulin (thyroid cancer) and fibrin/fibrin degradation protein (FDP) (bladder cancer).

The targets may also be gene products capable of providing a specific expression profile. For example in relation to metastasis phase of a tumor it is known that a specific gene expression profile may be found. By the present method it is possible to identify a gene expression profile and thereby determine the metastatic properties of a tumor or a metastasis found in a lymph node.

The targets may be detected directly, for example by using a primary antibody, or secondary by using an appropriate secondary antibody (such as rabbit anti-mouse IgG when using mouse primary antibodies) and/or a tertiary avidin (or Strepavidin) biotin complex ("ABC").

Examples of staining substances (also termed stains) include various enzymes, prosthetic groups, fluorescent materials, luminescent materials, bioluminescent materials, radioactive materials, positron emitting metals using various positron emission tomographies, and non-radioactive paramagnetic metal ions. The staining substance may be coupled or conjugated either directly to an antibody (or fragment thereof) or indirectly, through an intermediate (such as, for example, a linker known in the art) using techniques known in the art. Examples of labels that can be used include but are not limited to radiolabels such as $^{3}$H, $^{14}$C, $^{32}$P, $^{125}$I, $^{131}$I, $^{111}$In or $^{99}$Tc; fluorescent labels such as fluorescein and its derivatives, rhodamine and its derivatives, dansyl and umbelliferone; chemiluminescers such as luciferase and 2,3-dihydrophthalazinediones; and enzymes such as horseradish peroxidase, alkaline phosphatase, lysozyme, glucose-6-phosphate dehydrogenase, and acetylcholinesterase. Antibodies can be tagged with such stains by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels. The general methods involved are well known in the art. Specific examples of staining substances are e.g. antibodies against HER2/neu such as e.g the Herceptest from Dako, Pathway from Ventana and Novocastra from Novocastra Laboratories Ltd. Other example of staining substance is Vysis® LSI® TOP2A SpectrumOrange/HER-2 SpectrumGreen/CEP® 17 SpectrumAqua™ Probe from Abbott.

In another embodiment the targets may be nucleotides, such as detection of mutations in genes, for example point mutations. A specific binding between the target and the stain may be provided by a nucleotide probe being complementary to the nucleotide sequence to be detected. A staining molecule as discussed above may be coupled to the nucleotide probe by means as described above.

It is preferred that the sample is illuminated during acquisition of the digital representations, such as by using UV or illumination visible to the human eye.

Targets Associated with Cell Membranes

In one embodiment of the present invention the targets are associated with the cell membranes, such as receptors attached to the cell membrane. When the targets are stained the staining will appear as lines defining the cell membranes, see for example FIG. 1a. Any target associated with a cell membrane and capable of being stained may be identified using the present invention. Furthermore, the targets may also be quantified for example by determining the staining intensity, as described above, such as for example determination of chromaticity value, such as the red chromaticity and/or normalized brown, see above. Thus, the present invention allows for grading of the cell sample, wherein the grading may relate to the amount of targets present in the sample.

Example 1 shows an example of identifying stained targets associated with cell membranes, determination of the staining intensity and subsequent grading of the cell samples.

As discussed above, connectivity is also a measure that has proved to contribute (statistically) independent information about the patients disease status. Connectivity is relates to the area of membranes divided with the number of connected membranes, it membranes exhibiting a continuity in the image.

Furthermore, the various measures may be combined, such as a combination of chromaticity value and connectivity.

Targets Associated with Extracellular Linear Structures

In one embodiment of the present invention the targets are associated with linear structures outside the cell, such as receptors lining vessels or bronchi. When the targets are stained the staining will appear as lines defining the structures. Any target associated with a linear structure and capable of being stained may be identified using the present invention. Furthermore, the targets may also be quantified for example by determining the staining intensity, as described above. Thus, the present invention allows for grading of the cell sample, wherein the grading may relate to the amount of targets present in the sample.

Blob-Shaped Targets

Blob-shaped targets are targets being concentrated as a blob, for example targets being concentrated in small areas of the cell, such as in lyzosomes or the like, or such as detection of mutations in a gene, for example wherein only one target may be present per cell.

Blob-shaped targets may range from a single molecule corresponding to only a few pixels in the digital representation, to larger blobs giving rise to signals on several or many pixels, such as high locally arranged molecule concentrations, cell nuclei, whole cells, organelles or blob-shaped tissue structures.

Example 2 shows an example of identifying stained blob-shaped targets.

Diseases

The present invention may be applied to cell samples relating to a variety of diseases wherein a marker present in or on a cell is identifiable. Accordingly, the cell sample may originate from body fluids or tissue samples relating to for example the following diseases:

Breast cancer, gastrointestinal cancer, ovarian cancer, colorectal cancer, prostate cancer, retinoblastoma, lung cancer such as small cell lung cancer, skin tumors such as melanoma, nasopharyngeal tumors, bladder cancer, pancreatic cancer, testis cancer, nonseminoma testicular cancer, thyroid cancer, lymphoma, carcinoma in general.

In one embodiment the methods according to the invention may also be used for identifying whether a lymph node comprises metastatic tissue from a tumor, for example the first lymph node downstream from the tumor.

In one aspect the invention further relates to a method of classifying the sample based on the information obtained in the identification method discussed above. Accordingly, once stained targets in the sample has been identified the sample may be classified, for example classified as belonging to one of several classes as is the case in relation to cancer diagnostics, wherein the sample as discussed in the examples is allocated to one group or another depending on for example intensity and/or connectivity. Classification may be carried out using any suitable statistical means.

In one embodiment a general method of grouping the samples is based on classical multivariate discriminant analysis, such as a linar or quadratic Bayesian classifier, and regularized discriminant analysis, and in particular linear discriminant analysis, and quadratic discriminant analysis. By using such classifiers outliers qare easily identified as having a low probability of belonging to any of the identified groups. Sometimes, this is referred to as a "reject class" in the literature. The method may also include an "outlier warning", ie. a warning that the sample seems to fit in neither of the defined groups, wherein the user of the system is warned that the sample represents problems, such as not comprising relevant tissue or the like. In one embodiment, only two features are used: Connectivity and staining intensity.

Classical discriminant analysis is described in e.g. "En introduction til Statistic, vol 2B, Knut Contadsen, IMM".

In another embodiment of classifying a sample is based on Classification and Regression Trees, as described in "Classification And Regression Trees, Breiman, Friedman, Ohlsen, Stone, Chapman & Hall, 1993". The basic underlying principle is a binary split on the features extracted from the image. In one embodiment, a first split is made on the connectivity feature thus splitting samples in "Positive" and "Negative". These two groups are then further split into classical diagnostic scores based on their intensity.

The digital representation may be acquired by any suitable method and system. In preferred embodiments, target staining is detected, measured and quantified using image analysis equipment, defined herein as for example comprising a light or fluorescence microscope, image-transmitting camera, or a virtual microscope (slide scanner) and a view screen, most preferably also comprising a computer that can be used to direct the operation of the device and also store and manipulate the information collected, most preferably in the form of optical density of certain regions of a stained tissue preparation. Image analysis devices useful in the practice of this invention include but are not limited to the system described in PCT/DK2007/050171.

In another aspect, the present invention further encompasses an automated or semi-automated system suitable for carrying out one or more of the methods disclosed herein, said automated or semi-automated system comprising, in combination:
a database capable of including a plurality of digital representations of a plurality of biological specimens;
a software module for analyzing a plurality of pixels from a digital representation of a biological specimen;
a control module comprising instructions for carrying out said method(s).

Said automated or semi-automated system can also further comprise one or more of: a slide loader, a barcode reader, a microscope (preferably motorized), and a stage (preferably motorized).

For example, the microscope can include motorized stage, an automated apparatus for focusing, for changing lens objectives between high and low magnification, and for adjustment of the light incident of the slide, as well as circuitry for controlling the movement of the motorized stage, typically in response to a command from the processing system. The microscope may also include an automated slide transport system for moving the slides containing the specimen to be classified on to and off of the motorized stage, and a bar code reader for reading encoded information from the slide. An example of a microscope performing at least some of these functions is manufactured by Carl Zeiss, Inc. of Germany, Leica Microsystems, Nikon, or Olympus. Several automated slide loaders are commercially available today, allowing for the automated loading of slides onto a motorized stage mounted on a microscope. Suitable systems are e.g. supplied by Ludl or Prior. Such loaders can be controlled by standard Windows based computers, and fittet to most standard research microscopes. They generally have the ability to hold 50+ slides, and some of them are fitted to read a range of bar-code symbologies.

Integrating such a loader with the system allows unattended, high-volume sampling and digitization of microscopy slides, and with the application of bar-codes data management at a very high level can be fully integrated into the work process.

Using a fully automated microscope, it is possible to let the system switch between low and high magnification. By using low magnification, it is possible to obtain a "superlens" representation providing an overview of the entire slide, and let the system automatically identify regions on the slide containing tissue, using image analysis.

The system may further include a general processor and peripherals for printing, storage, etc. The general processor can be a microprocessor based microcomputer, although it may be another computer-type device suitable for efficient execution of the functions described herein. The general processor can for example control the functioning and the flow of data between components of the device, and handles the storage of representation and classification information. The general processor can additionally control peripheral devices such as a printer, a storage device, such as an optical or magnetic hard disk, a tape drive, etc., as well as other devices including a bar code reader, a slide marker, autofocus circuitry, a robotic slide handler, the stage, and a mouse.

Preferably, the representations obtained are monochrome representations, color representations, or multi-frame (e.g. multispectral) representations. Representations are preferably stored as TIFF representations, or as JPEG or other standard formats.

In another embodiment the digital representation may be acquired from a virtual slide obtained by means of a virtual microscope imaging the cell sample in question. In this embodiment, the entire tissue area has been scanned at high magnification in e.g. a virtual slide scanner, and the resulting representation is already stored, for example on the harddisk. The system now handles this large representation as if it was controlling a microscope, stage, camera etc. Thus, the user can use the exact same interface to work with virtual microscope representations as when working with an actual microscope.

In another aspect the present invention relates to a method for providing a calibration curve. This is most generally accomplished by using cells, most preferably cultured cell lines, producing a consistent amount of the target that can be determined with high degrees of accuracy and precision. In preferred embodiments, a plurality of cell populations are assessed each expressing different amounts of the target. Such cell populations are used to determine the amount of target staining associated with varying amounts of target in the different cell populations. In the practice of the invention, the correlation between target staining and the amount of target expressed in a cell is expressed as a calibration curve relating the amount of target to a physical parameter, most preferably optical density, associated with target staining. The calibration curves produced according to and used with the methods of the invention are also advantageously expressed as an algorithm, most preferably in the form of a linear or logarithmic equation.

In yet another aspect the present invention provides a method for calibrating a system for identifying stained targets. For many applications both the identification of cells as well as the quantification of stained targets depends on a variety of parameters, such as the optics of the system, the light setting, the amount of staining used, the quality of staining used etc. Accordingly, in order to provide reliable results of the analysis of the cell sample it is of importance to evaluate and optionally calibrate systems regularly. In one aspect the calibration is carried out by performing the methods according to this invention using a standardized set of digital representations, in particular for evaluating the hardware settings of the system. The system is evaluated with respect to its ability of reproducing the correct results for identifying the stained targets and optionally also quantifying the stained targets.

In another aspect the parameters used, such as type and amount of staining, may be evaluated by staining either a standardized set of biological cell samples and performing the methods of identification and optionally quantification, or by staining a random set of biological cell samples and performing the methods of identification and optionally quantification on both the system to be evaluated and on a standardized system. Thereby it is possible to evaluate for example whether the correct amount of staining has been applied to the cell sample and the correct time for allowing the staining reactions to be performed. It is clear that too little staining or too much staining may lead to an incorrect identification as well as incorrect quantification of stained targets, thereby leading to an incorrect classification of the cell samples.

In the scenarios discussed above the calibration curve according to this invention may be used for evaluating the parameters and settings of the method and system.

Computer Readable Medium

In another aspect, the present invention further encompasses a computer readable medium comprising instructions for carrying out one or more of the methods disclosed herein. Suitable computer-readable media can for example be a hard disk to provide storage of data, data structures, computer-executable instructions, and the like. Other types of media which are readable by a computer, such as removable magnetic disks, CDs, magnetic cassettes, flash memory cards, digital video disks, and the like, may also be used.

EXAMPLES

Example 1a

Diagnostic Method for Breast Cancer

A set of 30 known cell samples were analysed according to the methods according to the invention, wherein a second-order polynomial was used in the filtering step.

The cell samples were all stained with a DAKO staining for HER2.

Each cell sample were analysed 5 times, except one that was only analysed four times. An average value was obtained for each cell sample. In table 1 the results are shown.

Figure 3A:
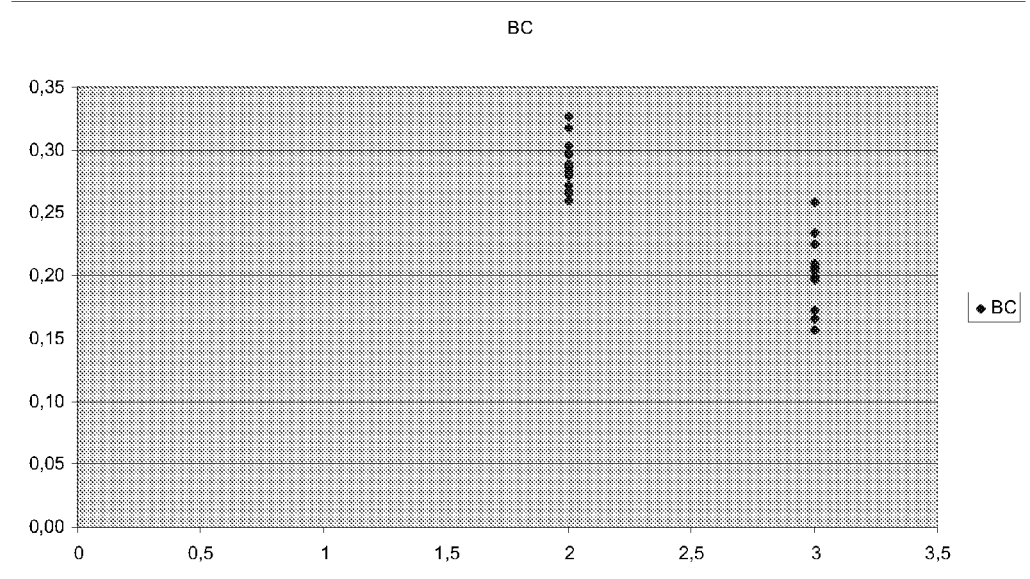
FIGS. 3a-c show the results of grading 30 tissue samples from breast cancer using the method according to the invention by scoring either blue chromaticity (a), red chromaticity (b) or saturation (c)]
Figure 3B:
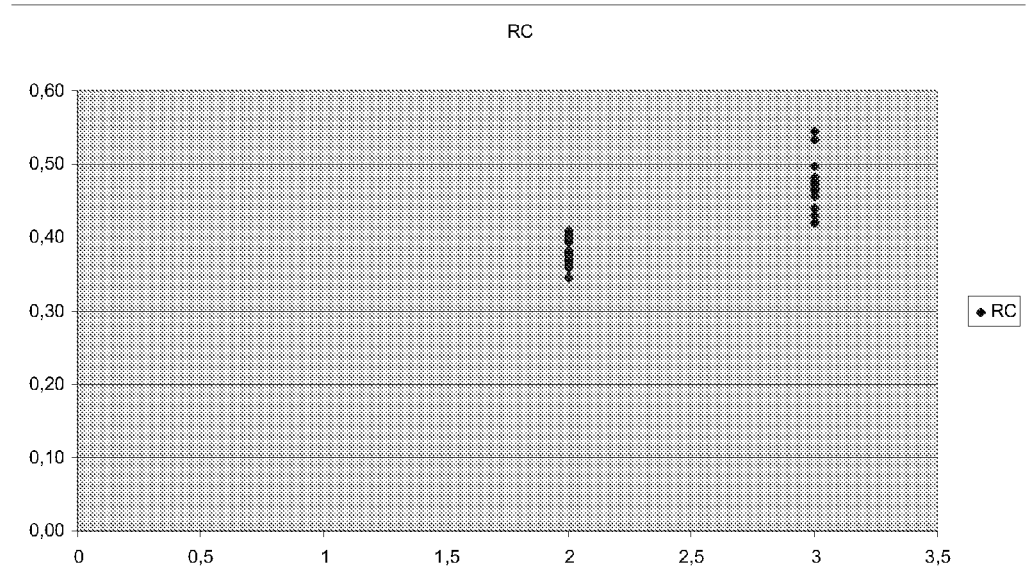
Figure 3C:
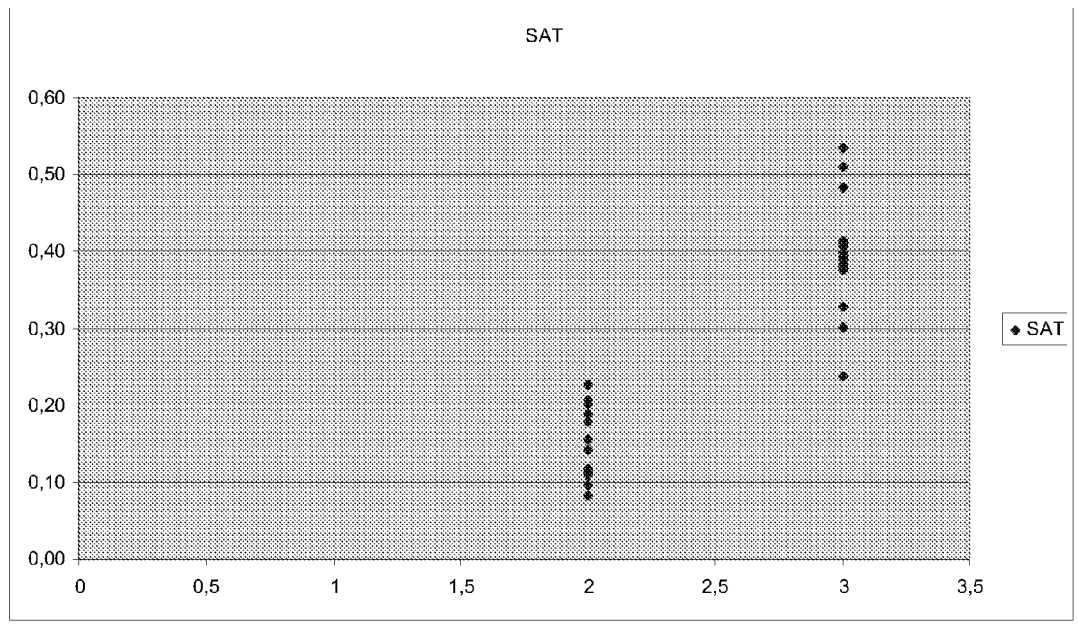

Furthermore, FIG. 3a-3c shows the correlation between red colour (RC), blue colour (BC), and saturation and the grade of the cell sample. It is seen that it is possible by the present method to classify the cell samples correctly. Grade 1 is a tumour with a good prognosis whereas grade 3 is a tumour with a poor prognosis.

TABLE 1

| Study Unit | Score | Measurement | ABC | ARC | SAT |
|---|---|---|---|---|---|
| H 4650 06 O 40x | 3 | 1 | 0.140305755 | 0.567683507 | 0.585557968 |
| H 4650 06 O 40x | 3 | 2 | 0.151161811 | 0.557879074 | 0.551546411 |
| H 4650 06 O 40x | 3 | 3 | 0.14499109 | 0.562841496 | 0.573876017 |
| H 4650 06 O 40x | 3 | 4 | 0.165196836 | 0.52702309 | 0.506042989 |
| H 4650 06 O 40x | 3 | 5 | 0.182473728 | 0.503168463 | 0.455627413 |
| H 12664 06 B 40x | 2 | 1 | 0.289148943 | 0.377945721 | 0.133820485 |
| H 12664 06 B 40x | 2 | 2 | 0.292537673 | 0.372403482 | 0.125716553 |
| H 12664 06 B 40x | 2 | 3 | 0.289834383 | 0.375007031 | 0.131340791 |
| H 12664 06 B 40x | 2 | 4 | 0.311560659 | 0.358334072 | 0.091828803 |
| H 12664 06 B 40x | 2 | 5 | 0.298739788 | 0.367848544 | 0.104750276 |
| H 11190 06 J 40x | 2 | 1 | 0.329677877 | 0.34808864 | 0.099567094 |
| H 11190 06 J 40x | 2 | 2 | 0.310383156 | 0.364080081 | 0.105611368 |
| H 11190 06 J 40x | 2 | 3 | 0.31277959 | 0.362776616 | 0.12463138 |
| H 11190 06 J 40x | 2 | 4 | 0.331907797 | 0.349275874 | 0.100380346 |
| H 11190 06 J 40x | 2 | 5 | 0.303526615 | 0.367602203 | 0.118081774 |
| H 11814 05 A 40x | 2 | 1 | 0.30872503 | 0.356608078 | 0.07782692 |
| H 11814 05 A 40x | 2 | 2 | 0.302595063 | 0.363145623 | 0.094440839 |
| H 11814 05 A 40x | 2 | 3 | 0.294105232 | 0.369438379 | 0.11926553 |
| H 11814 05 A 40x | 2 | 4 | 0.308142969 | 0.356703075 | 0.079978472 |
| H 11814 05 A 40x | 2 | 5 | 0.299503106 | 0.366127353 | 0.103437418 |
| H 12907 05 B 40x | 2 | 1 | 0.318690677 | 0.348493395 | 0.063654083 |
| H 12907 05 B 40x | 2 | 2 | 0.29088741 | 0.373213779 | 0.128868198 |
| H 12907 05 B 40x | 2 | 3 | 0.371845488 | 0.31328339 | 0.102853527 |
| H 12907 05 B 40x | 2 | 4 | 0.318884914 | 0.347447997 | 0.057761714 |
| H 12907 05 B 40x | 2 | 5 | 0.331902285 | 0.338986559 | 0.05583704 |
| H 8212 06 A 40x | 2 | 1 | 0.269985264 | 0.391596274 | 0.190342601 |
| H 8212 06 A 40x | 2 | 2 | 0.2818506 | 0.381505677 | 0.155941809 |
| H 8212 06 A 40x | 2 | 3 | 0.291310272 | 0.373774788 | 0.129128588 |
| H 8212 06 A 40x | 2 | 4 | 0.284903417 | 0.381298241 | 0.147392346 |
| H 8212 06 A 40x | 2 | 5 | 0.284313574 | 0.378709552 | 0.149573478 |
| H 8430 05 D 40x | 3 | 1 | 0.220128593 | 0.449771768 | 0.341499255 |
| H 8430 05 D 40x | 3 | 2 | 0.21602808 | 0.455042192 | 0.354338333 |
| H 8430 05 D 40x | 3 | 3 | 0.207081254 | 0.461939725 | 0.380258942 |
| H 8430 05 D 40x | 3 | 4 | 0.202042296 | 0.466157139 | 0.395570719 |
| H 8430 05 D 40x | 3 | 5 | 0.186272044 | 0.485685944 | 0.442756881 |
| H 10222 05 B 40x | 3 | 1 | 0.20320171 | 0.469126019 | 0.39278817 |
| H 10222 05 B 40x | 3 | 2 | 0.203162365 | 0.47419604 | 0.394844649 |
| H 10222 05 B 40x | 3 | 3 | 0.196486159 | 0.480168642 | 0.413802753 |
| H 10222 05 B 40x | 3 | 4 | 0.189671544 | 0.489105956 | 0.434415171 |
| H 10222 05 B 40x | 3 | 5 | 0.191102904 | 0.488797499 | 0.431137095 |
| H 6358 06 B 40x | 3 | 1 | 0.150253965 | 0.558724867 | 0.557084024 |
| H 6358 06 B 40x | 3 | 2 | 0.178672411 | 0.523306517 | 0.474585608 |
| H 6358 06 B 40x | 3 | 3 | 0.157711048 | 0.537353875 | 0.53165111 |
| H 6358 06 B 40x | 3 | 4 | 0.16595881 | 0.52868736 | 0.509417395 |
| H 6358 06 B 40x | 3 | 5 | 0.175191638 | 0.512331875 | 0.481347277 |
| H 22475 05 H 40x | 3 | 1 | 0.195962869 | 0.474760526 | 0.416017729 |
| H 22475 05 H 40x | 3 | 2 | 0.199597174 | 0.471095892 | 0.405727144 |
| H 22475 05 H 40x | 3 | 3 | 0.198193245 | 0.467701857 | 0.407815319 |
| H 22475 05 H 40x | 3 | 4 | 0.213086998 | 0.457734082 | 0.365583598 |
| H 22475 05 H 40x | 3 | 5 | 0.211296966 | 0.454381596 | 0.36828678 |
| H 11829 05 A 40x | 3 | 1 | 0.159795697 | 0.507786892 | 0.521505738 |
| H 11829 05 A 40x | 3 | 2 | 0.172249822 | 0.500165834 | 0.485185894 |
| H 11829 05 A 40x | 3 | 3 | 0.173029912 | 0.491409823 | 0.481595337 |
| H 11829 05 A 40x | 3 | 4 | 0.189604103 | 0.483853618 | 0.434177908 |
| H 11829 05 A 40x | 3 | 5 | 0.168216371 | 0.502042579 | 0.496929264 |
| H 12382 05 C 40x | 3 | 1 | 0.205618079 | 0.473458353 | 0.391156709 |
| H 12382 05 C 40x | 3 | 2 | 0.199398618 | 0.478800795 | 0.408408108 |
| H 12382 05 C 40x | 3 | 3 | 0.21710658 | 0.463320369 | 0.356559746 |
| H 12382 05 C 40x | 3 | 4 | 0.20960678 | 0.475403866 | 0.38273506 |
| H 12382 05 C 40x | 3 | 5 | 0.183849643 | 0.500065892 | 0.453851936 |
| H 11806 05 J 40x | 3 | 1 | 0.203283314 | 0.45588912 | 0.391076567 |
| H 11806 05 J 40x | 3 | 2 | 0.196744194 | 0.466754742 | 0.411288292 |

TABLE 1-continued

| Study Unit | Score | Measurement | ABC | ARC | SAT |
|---|---|---|---|---|---|
| H 11806 05 J 40x | 3 | 3 | 0.205551198 | 0.462144208 | 0.385715167 |
| H 11806 05 J 40x | 3 | 4 | 0.213007946 | 0.452398271 | 0.362783818 |
| H 11806 05 J 40x | 3 | 5 | 0.217614791 | 0.445272342 | 0.349399744 |
| H 11722 05 A 40x | 3 | 1 | 0.219002716 | 0.449313366 | 0.347731229 |
| H 11722 05 A 40x | 3 | 2 | 0.222866305 | 0.438887275 | 0.333604573 |
| H 11722 05 A 40x | 3 | 3 | 0.230230346 | 0.432447089 | 0.312284847 |
| H 11722 05 A 40x | 3 | 4 | 0.248358799 | 0.412072496 | 0.255467957 |
| H 11722 05 A 40x | 3 | 5 | 0.250379981 | 0.41791637 | 0.253545763 |
| H 17844 06 C 40x | 3 | 1 | 0.222292084 | 0.451961026 | 0.335998944 |
| H 17844 06 C 40x | 3 | 2 | 0.202035146 | 0.47425487 | 0.397728822 |
| H 17844 06 C 40x | 3 | 3 | 0.201253726 | 0.47473401 | 0.40000563 |
| H 17844 06 C 40x | 3 | 4 | 0.216225279 | 0.458464477 | 0.353899458 |
| H 17844 06 C 40x | 3 | 5 | 0.205067037 | 0.473600552 | 0.388624495 |
| H 11726 05 B 40x | 2 | 1 | 0.298271537 | 0.36698968 | 0.110033235 |
| H 11726 05 B 40x | 2 | 2 | 0.2842417 | 0.379561738 | 0.14811903 |
| H 11726 05 B 40x | 2 | 3 | 0.277563962 | 0.384615481 | 0.168062631 |
| H 11726 05 B 40x | 2 | 4 | 0.287125621 | 0.377043449 | 0.146115718 |
| H 11726 05 B 40x | 2 | 5 | 0.265134431 | 0.399042203 | 0.20628677 |
| H 10952 03 A 40x | 3 | 1 | 0.184967411 | 0.48609024 | 0.446111995 |
| H 10952 03 A 40x | 3 | 2 | 0.192790187 | 0.478772553 | 0.424700299 |
| H 10952 03 A 40x | 3 | 3 | 0.19794829 | 0.473258649 | 0.4086401 |
| H 10952 03 A 40x | 3 | 4 | 0.200437046 | 0.467097778 | 0.399956788 |
| H 10952 03 A 40x | 3 | 5 | 0.216579815 | 0.450142341 | 0.352215743 |
| H 5817 04 G 40x | 2 | 1 | 0.301166424 | 0.367159426 | 0.106130239 |
| H 5817 04 G 40x | 2 | 2 | 0.301575034 | 0.364589156 | 0.10021868 |
| H 5817 04 G 40x | 2 | 3 | 0.297012722 | 0.369092713 | 0.119559203 |
| H 5817 04 G 40x | 2 | 4 | 0.29800526 | 0.368204571 | 0.116936954 |
| H 5817 04 G 40x | 2 | 5 | 0.292247953 | 0.373160534 | 0.128561639 |
| H 8865 05 F 40x | 2 | 1 | 0.241927844 | 0.426840153 | 0.27883397 |
| H 8865 05 F 40x | 2 | 2 | 0.25824932 | 0.408350334 | 0.227945106 |
| H 8865 05 F 40x | 2 | 3 | 0.265280237 | 0.402178978 | 0.208689023 |
| H 8865 05 F 40x | 2 | 4 | 0.273876257 | 0.393193859 | 0.182303245 |
| H 8865 05 F 40x | 2 | 5 | 0.257352951 | 0.412421194 | 0.233259023 |
| H 9119 05 D 40x | 3 | 1 | 0.174901586 | 0.507571944 | 0.477875706 |
| H 9119 05 D 40x | 3 | 2 | 0.202752305 | 0.477618456 | 0.397791971 |
| H 9119 05 D 40x | 3 | 3 | 0.204345495 | 0.477318959 | 0.392699298 |
| H 9119 05 D 40x | 3 | 4 | 0.230819421 | 0.450055886 | 0.314668869 |
| H 9119 05 D 40x | 3 | 5 | 0.217002712 | 0.469372404 | 0.36163233 |
| H 10715 05 A 40x | 2 | 1 | 0.291148963 | 0.383435477 | 0.154143582 |
| H 10715 05 A 40x | 2 | 2 | 0.282437044 | 0.391072691 | 0.168642801 |
| H 10715 05 A 40x | 2 | 3 | 0.291924397 | 0.381190819 | 0.148297478 |
| H 10715 05 A 40x | 2 | 4 | 0.268868179 | 0.403949119 | 0.206289316 |
| H 10715 05 A 40x | 2 | 5 | 0.265657964 | 0.408430692 | 0.217770538 |
| H 14945 05 D 40x | 3 | 1 | 0.228908859 | 0.436912465 | 0.317034812 |
| H 14945 05 D 40x | 3 | 2 | 0.213792659 | 0.450036951 | 0.362187072 |
| H 14945 05 D 40x | 3 | 3 | 0.230156375 | 0.43062817 | 0.312041316 |
| H 14945 05 D 40x | 3 | 4 | 0.224409264 | 0.440552743 | 0.331385199 |
| H 14945 05 D 40x | 3 | 5 | 0.227695279 | 0.433836016 | 0.31996661 |
| H 15042 05 G 40x | 2 | 1 | 0.29583216 | 0.36725936 | 0.113896356 |
| H 15042 05 G 40x | 2 | 2 | 0.289672819 | 0.371765773 | 0.132547283 |
| H 15042 05 G 40x | 2 | 3 | 0.287081425 | 0.374626163 | 0.140283254 |
| H 15042 05 G 40x | 2 | 4 | 0.28865984 | 0.372701995 | 0.134652433 |
| H 15042 05 G 40x | 2 | 5 | 0.271806219 | 0.392465418 | 0.185780876 |
| H 7098 06 A 40x | 3 | 1 | 0.195878937 | 0.47618724 | 0.416877152 |
| H 7098 06 A 40x | 3 | 2 | 0.206356238 | 0.458938076 | 0.382339894 |
| H 7098 06 A 40x | 3 | 3 | 0.192499047 | 0.474694197 | 0.424720389 |
| H 7098 06 A 40x | 3 | 4 | 0.199909078 | 0.472256051 | 0.403440807 |
| H 7098 06 A 40x | 3 | 5 | 0.192738081 | 0.481664712 | 0.42483259 |
| H 6527 06 B 40x | 2 | 1 | 0.273418075 | 0.393712517 | 0.184539227 |
| H 6527 06 B 40x | 2 | 2 | 0.263329595 | 0.400435293 | 0.211960765 |
| H 6527 06 B 40x | 2 | 3 | 0.265325694 | 0.401007473 | 0.205918351 |
| H 6527 06 B 40x | 2 | 4 | 0.264939522 | 0.401250768 | 0.208643966 |
| H 6527 06 B 40x | 2 | 5 | 0.270099081 | 0.393861554 | 0.193270683 |
| H 7317 06 A 40x | 3 | 1 | 0.256799814 | 0.417619823 | 0.239548511 |
| H 7317 06 A 40x | 3 | 2 | 0.244048238 | 0.433914524 | 0.278686443 |
| H 7317 06 A 40x | 3 | 3 | 0.248967165 | 0.430928969 | 0.263236241 |
| H 7317 06 A 40x | 3 | 4 | 0.283980602 | 0.393214075 | 0.169838338 |
| H 11352 06 D 40x | 2 | 1 | 0.303330724 | 0.363630697 | 0.092935256 |
| H 11352 06 D 40x | 2 | 2 | 0.306055868 | 0.36126552 | 0.092599157 |
| H 11352 06 D 40x | 2 | 3 | 0.296844913 | 0.369617522 | 0.118739232 |
| H 11352 06 D 40x | 2 | 4 | 0.291740809 | 0.374387005 | 0.125719177 |
| H 11352 06 D 40x | 2 | 5 | 0.290331189 | 0.373914984 | 0.133529355 |
| H 11090 06 C 40x | 2 | 1 | 0.26144462 | 0.406075197 | 0.218903503 |
| H 11090 06 C 40x | 2 | 2 | 0.274180245 | 0.390271194 | 0.180417925 |
| H 11090 06 C 40x | 2 | 3 | 0.272621456 | 0.391533093 | 0.18335394 |
| H 11090 06 C 40x | 2 | 4 | 0.266492356 | 0.401398527 | 0.202728217 |
| H 11090 06 C 40x | 2 | 5 | 0.282473493 | 0.384371374 | 0.154620693 |
| H 13035 06 C 40x | 2 | 1 | 0.275450451 | 0.390620895 | 0.175340271 |

TABLE 1-continued

| Study Unit | Score | Measurement | ABC | ARC | SAT |
|---|---|---|---|---|---|
| H 13035 06 C 40x | 2 | 2 | 0.284588958 | 0.382158062 | 0.150547389 |
| H 13035 06 C 40x | 2 | 3 | 0.283183158 | 0.384694148 | 0.161380194 |
| H 13035 06 C 40x | 2 | 4 | 0.304996164 | 0.362969751 | 0.099189372 |
| H 13035 06 C 40x | 2 | 5 | 0.294567178 | 0.372374012 | 0.124176044 |
| H 18862 06 A 40x | 2 | 1 | 0.260942008 | 0.408383572 | 0.221704201 |
| H 18862 06 A 40x | 2 | 2 | 0.269218561 | 0.398061776 | 0.195438986 |
| H 18862 06 A 40x | 2 | 3 | 0.266538675 | 0.405296572 | 0.205340154 |
| H 18862 06 A 40x | 2 | 4 | 0.265228482 | 0.400978097 | 0.206900393 |
| H 18862 06 A 40x | 2 | 5 | 0.264317323 | 0.400954955 | 0.208827032 |

Example 1b

Diagnostic Method for Breast Cancer

A set of 12 known cell samples were analysed according to the methods of the invention, wherein a second-order polynomial was used in the filtering step.

The cell samples were all stained with a cocktail of commercially available staining reagents for HER2.

Figure 4:
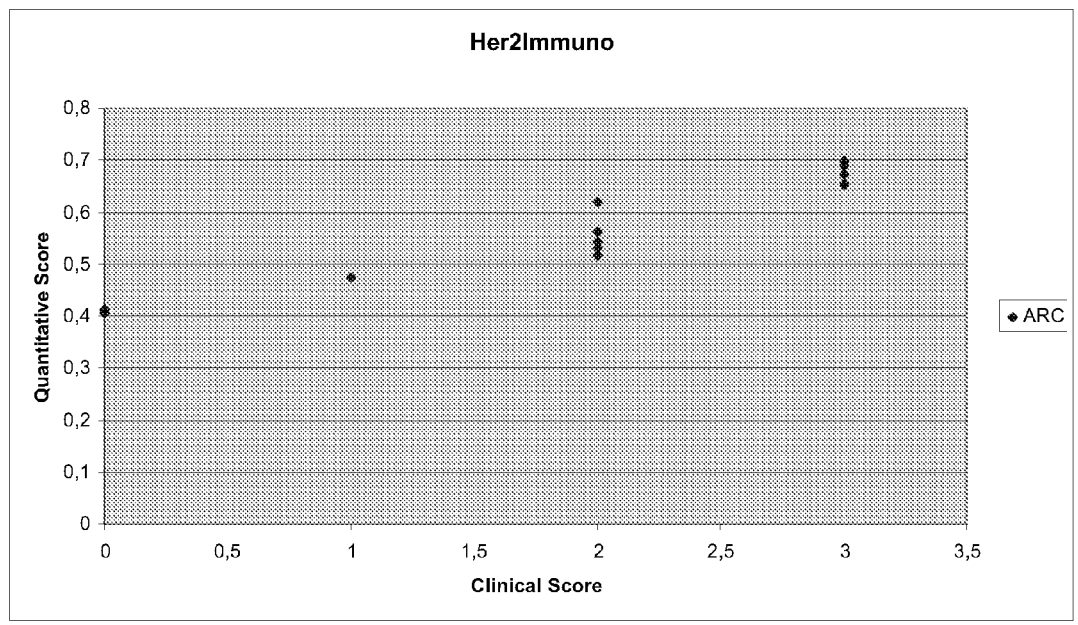
FIG. 4 shows the result of grading another set of tissue samples from breast cancer using the method according to the invention.

Table 2 shows the results for the cell samples, and FIG. 4 shows the correlation between the clinical score and the quantitative score.

Figure 5A:
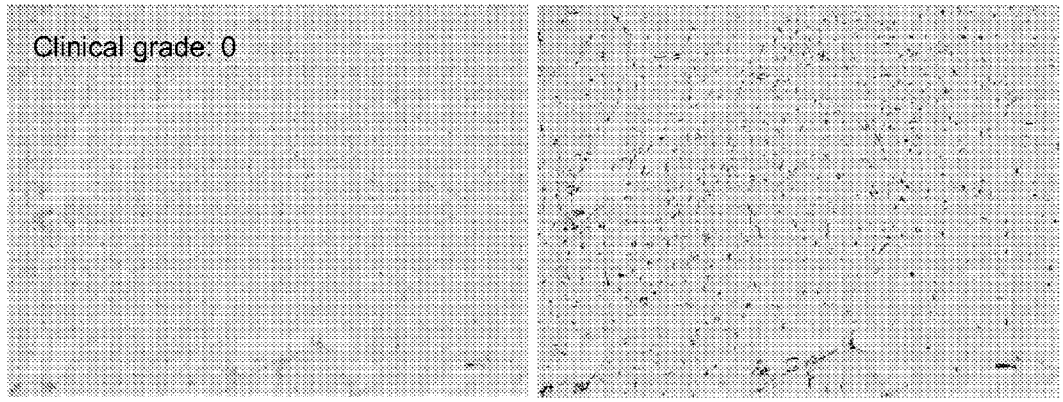
FIG. 5a-b show digital representations and segmented representations of tissue samples representing clinical grade 0, 1+ and 3+, wherein the digital representation is the left-hand representation.
Figure 5B:
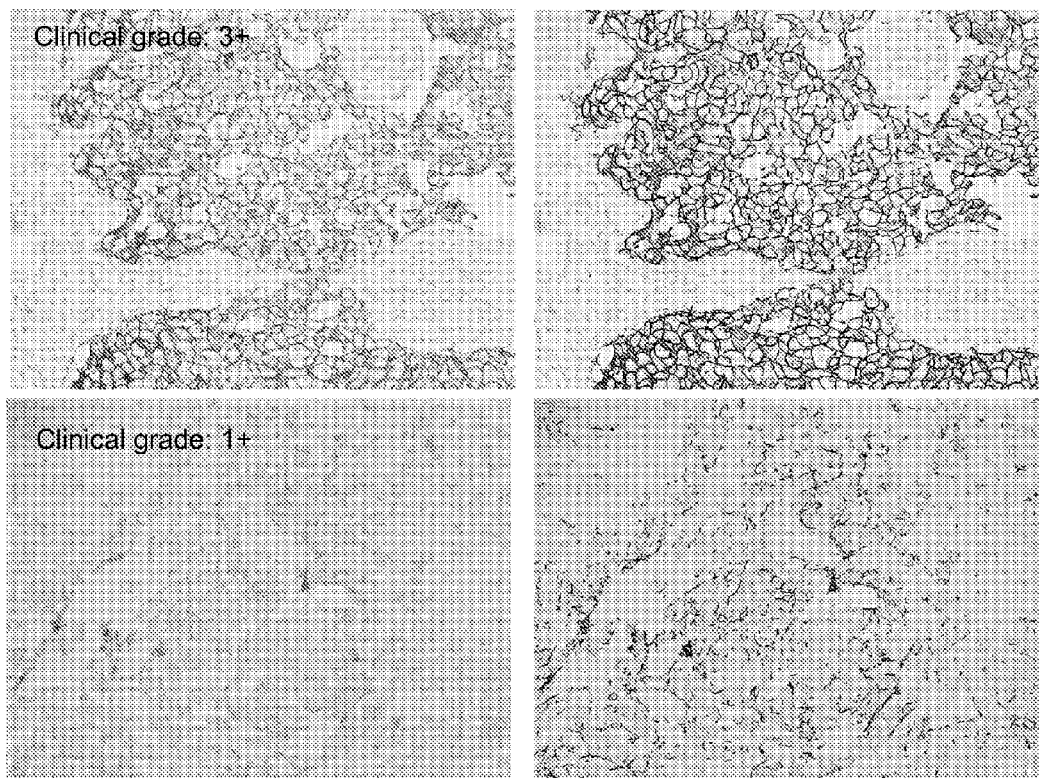

FIGS. 5a-b show the digital representations and the segmented representation, respectively, for clinical grad 0, 1+ and 3+. The digital representations are the left-hand representations.

TABLE 2

| Grade | ABC | AGC | ARC | Avg. Staining |
|---|---|---|---|---|
| 2 | 0.161488678 | 0.328537166 | 0.51562247 | 0.920557142 |
| 2 | 0.09887526 | 0.304347813 | 0.619136841 | 0.985191677 |
| 0 | 0.260744115 | 0.331384003 | 0.410530051 | 0.753248397 |
| 0 | 0.259839211 | 0.335294127 | 0.406137975 | 0.756244349 |
| 2 | 0.13852593 | 0.326704532 | 0.541695068 | 0.939668418 |
| 3 | 0.079267684 | 0.290178567 | 0.653341306 | 0.989884713 |
| 3 | 0.070623882 | 0.259615391 | 0.697310056 | 0.989889103 |
| 2 | 0.128698236 | 0.321285129 | 0.56101454 | 0.953971443 |
| 3 | 0.076289411 | 0.270370364 | 0.673424598 | 0.985081878 |
| 1 | 0.191981334 | 0.340292275 | 0.472722819 | 0.859086392 |
| 2 | 0.140973882 | 0.33502537 | 0.531151861 | 0.947177976 |
| 3 | 0.067544966 | 0.269360274 | 0.690039906 | 0.985041225 |

Example 2

Identification of Blob-Shaped Targets

Figure 6A:
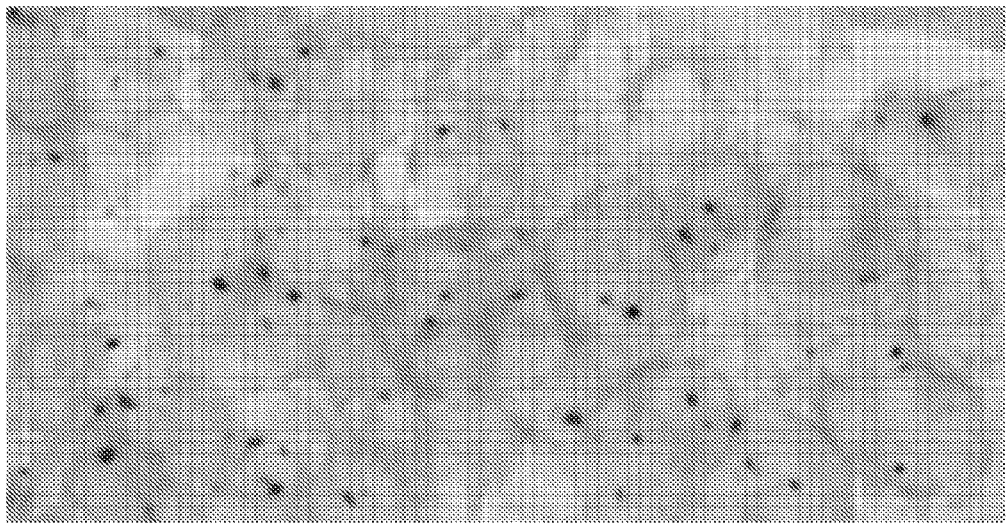
FIGS. 6a-6k shows the use of the methods according to the invention for identifying blob-shaped stained targets in a tissue sample.

FIG. 6a shows the digital representation of a cell sample wherein blob-shaped targets are stained. The digital representation is subjected to the filtering step of the present invention using a second-order polynomial.

Figure 6B:
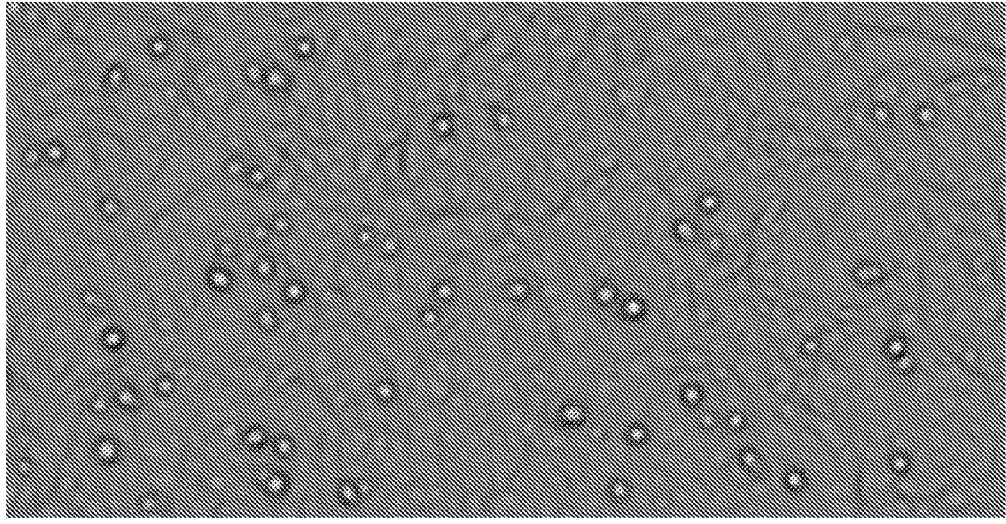

FIG. 6b shows the filtered representation wherein the second Eigen-value of Hessian Matrix is extracted from Green colour band.

Figure 6C:
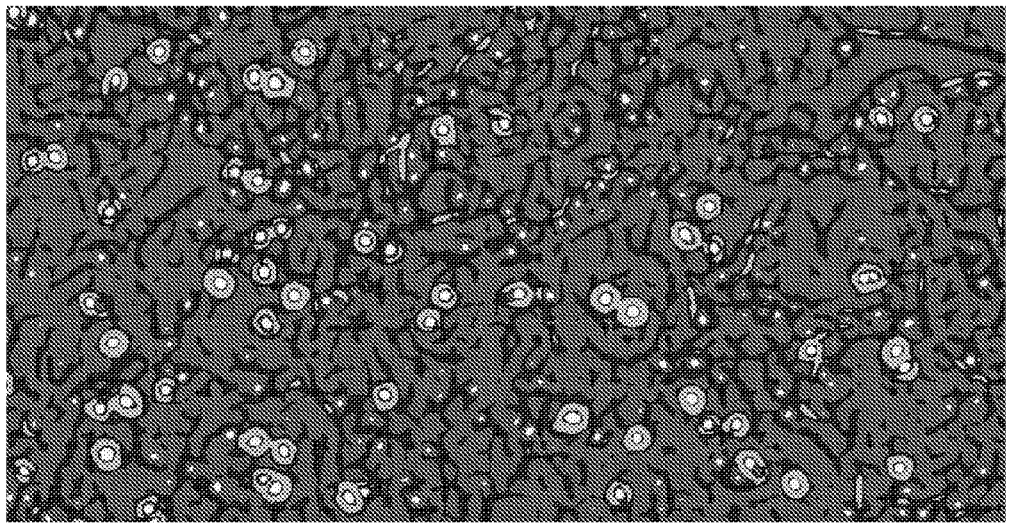

Then the segmentation step is initiated. FIG. 6c shows the responses, wherein Green is lowest response, Blue second lowest, Red, Second highest, Yellow Highest response.

Figure 6D:
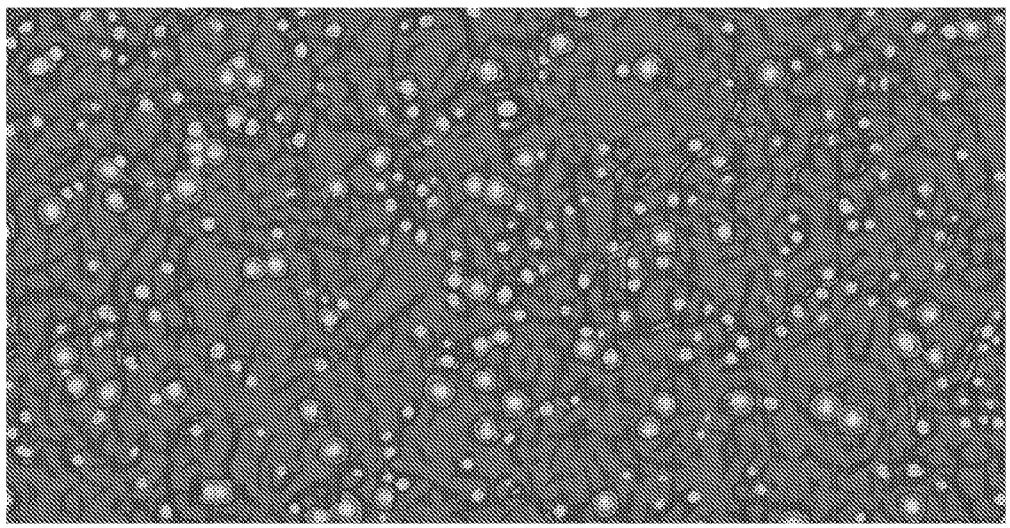

In FIG. 6d the highest response (yellow) is dilated to make sure it touches the Green halo (a sign that it is an admissible signal).

Figure 6E:
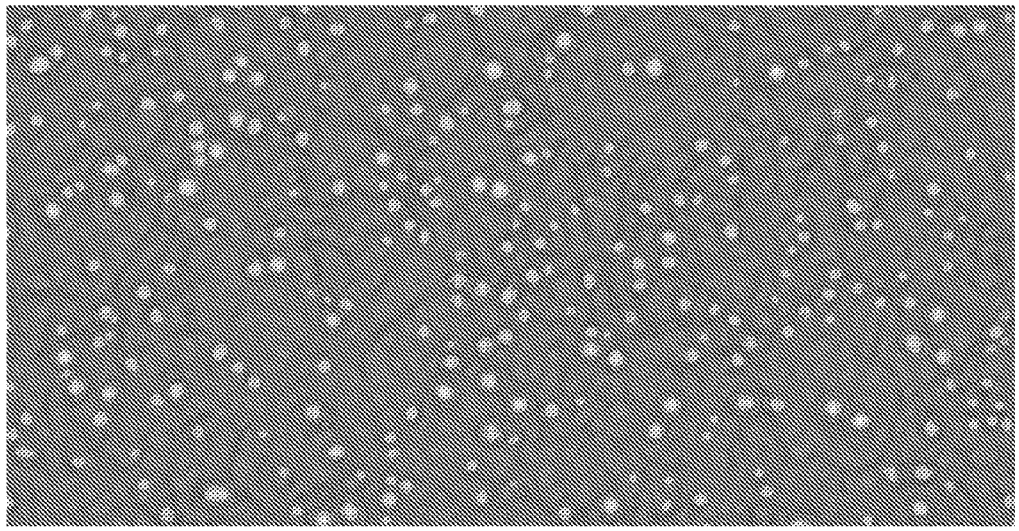

Background is removed in FIG. 6e, only signals with and without halos are preserved.

Figure 6F:
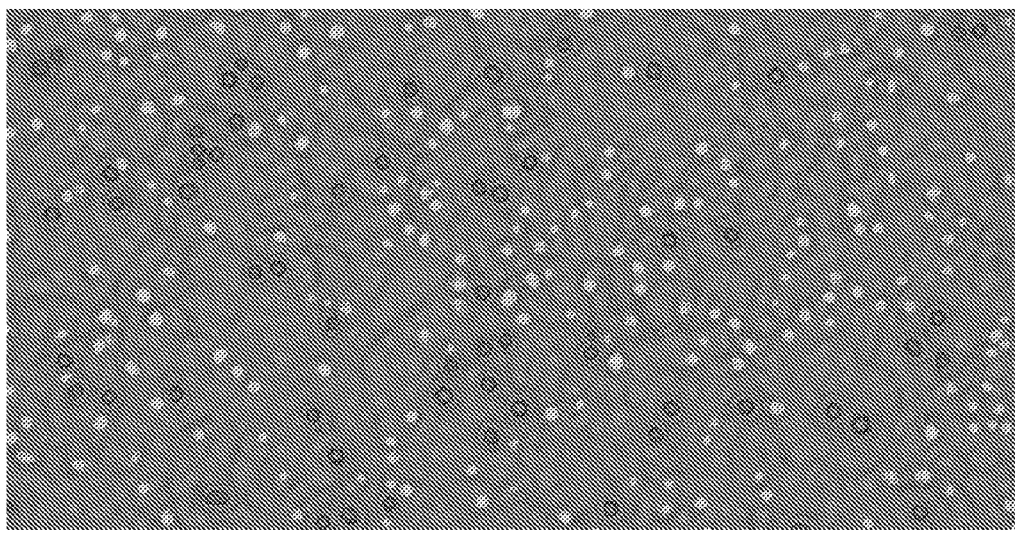
Figure 6G:
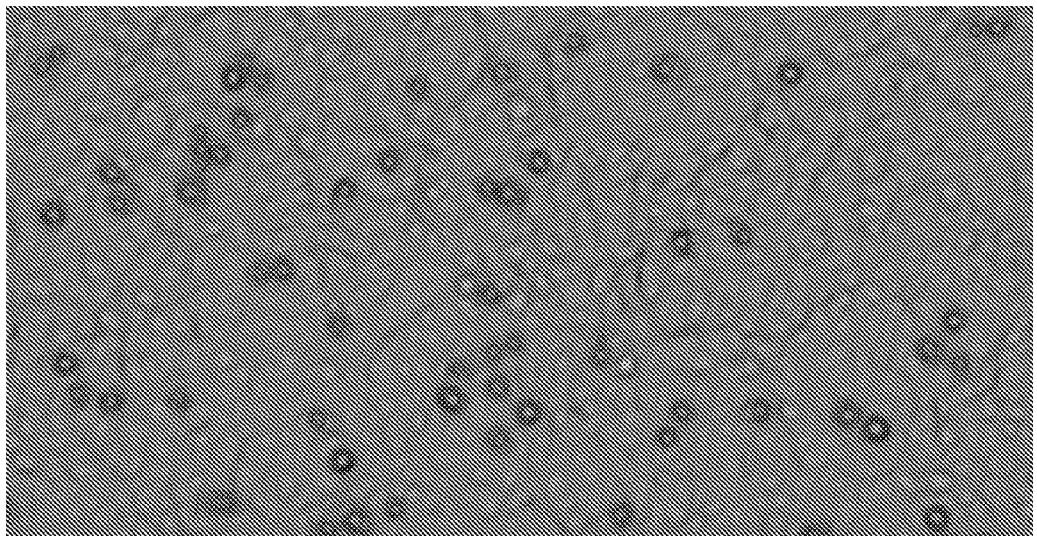

In FIG. 6f all cellular targets with a green halo is identified, and in FIG. 6g only the cellular targets with a halo are kept.

Figure 6H:
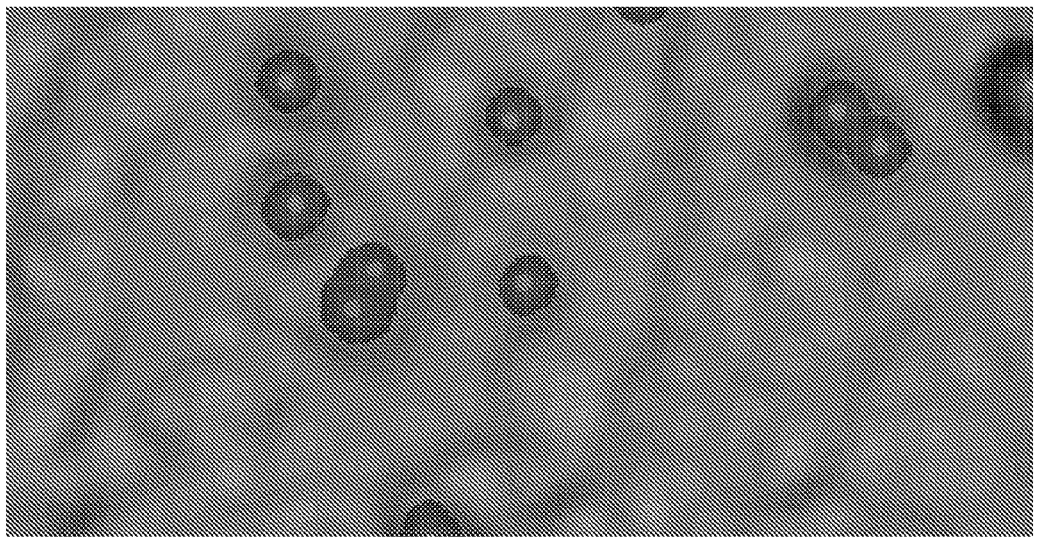

In FIG. 6h the filtered Eigen-value response is used to separate merged cellular targets, by identifying local extrema (maxima) in the response within an identified "object".

Figure 6I:
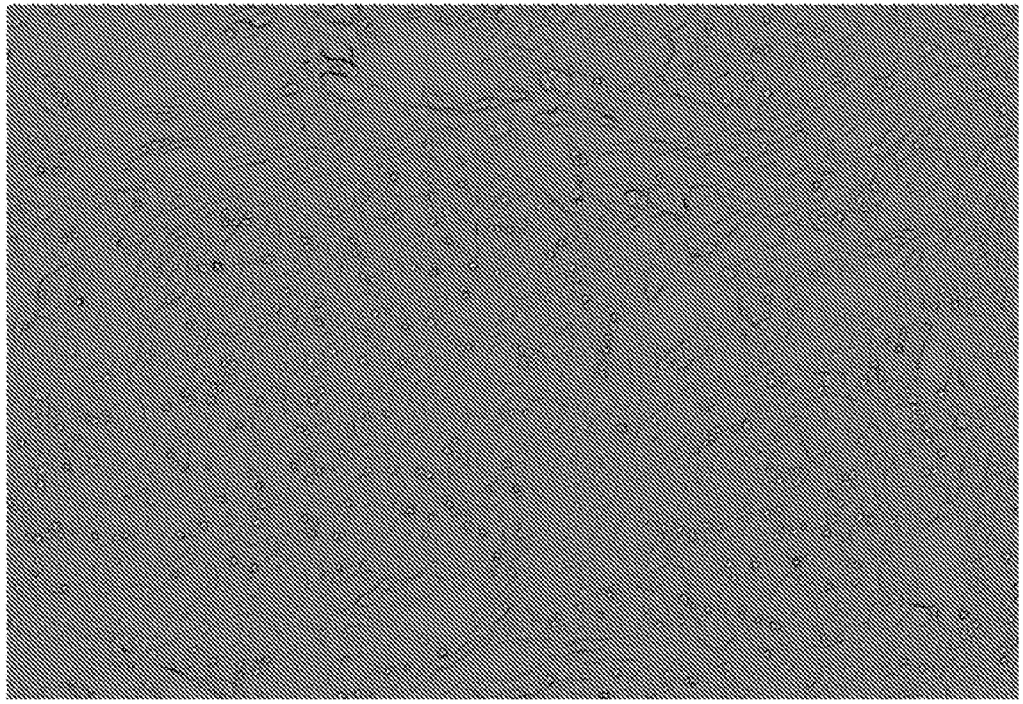

FIG. 6i shows all the identified stained targets.

Figure 6J:
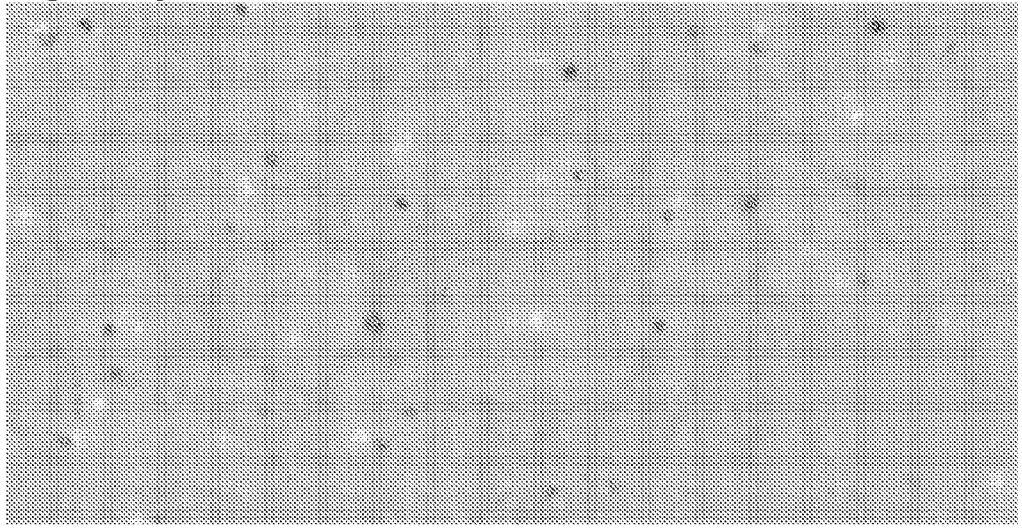

In FIG. 6j the red chromaticity is used to determine the type of a given cellular target. This is done by thresholding.

Figure 6K:
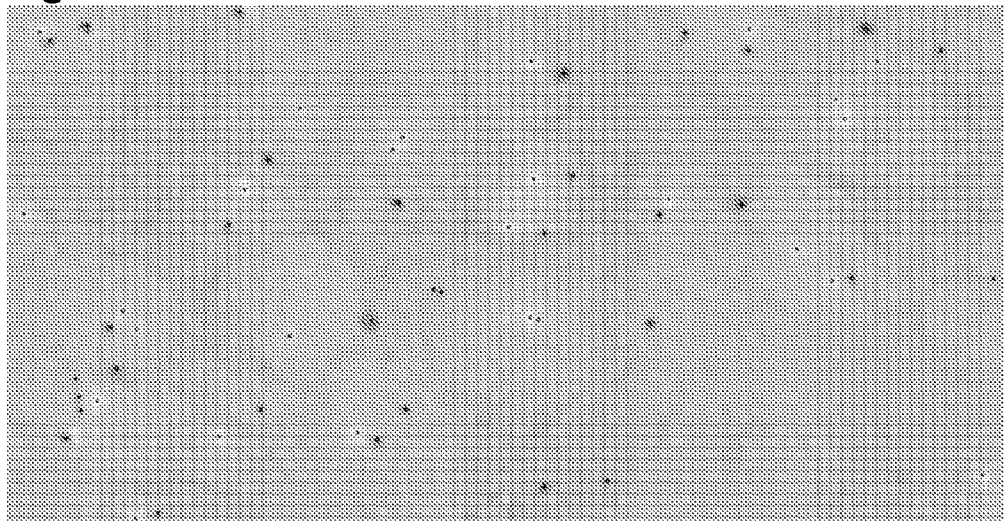

The result of the identification process is shown in FIG. 6k, wherein red stained targets and blue stained targets are shown. The result is then ready for quantification, such as counting of different types of cellular targets.

Example 3

Diagnosing Breast Cancer Using a Measure for Connectivity

On a set of known breast cancer samples analysed according to the methods of the invention a measure for connectivity was calculated. The breast cancer samples were stained with Herceptest and Pathway, respectively The measure for connectivity was calculated as the (log) average size of connected membrane objects, ie as the area of detected cell membranes divided with the number of connected cell membrane objects in the image, computed as log(1+AMEM/NMEM).

Adding 1 under the log operator is performed to safeguard computations for in case the area and number of objects may become zero. In such cases, the connectivity is defined as zero.

The purpose of the connectivity measure is to discriminate between Negative cases (0, and +1) and Positive cases (+3 and possibly +2).

Figure 7A:
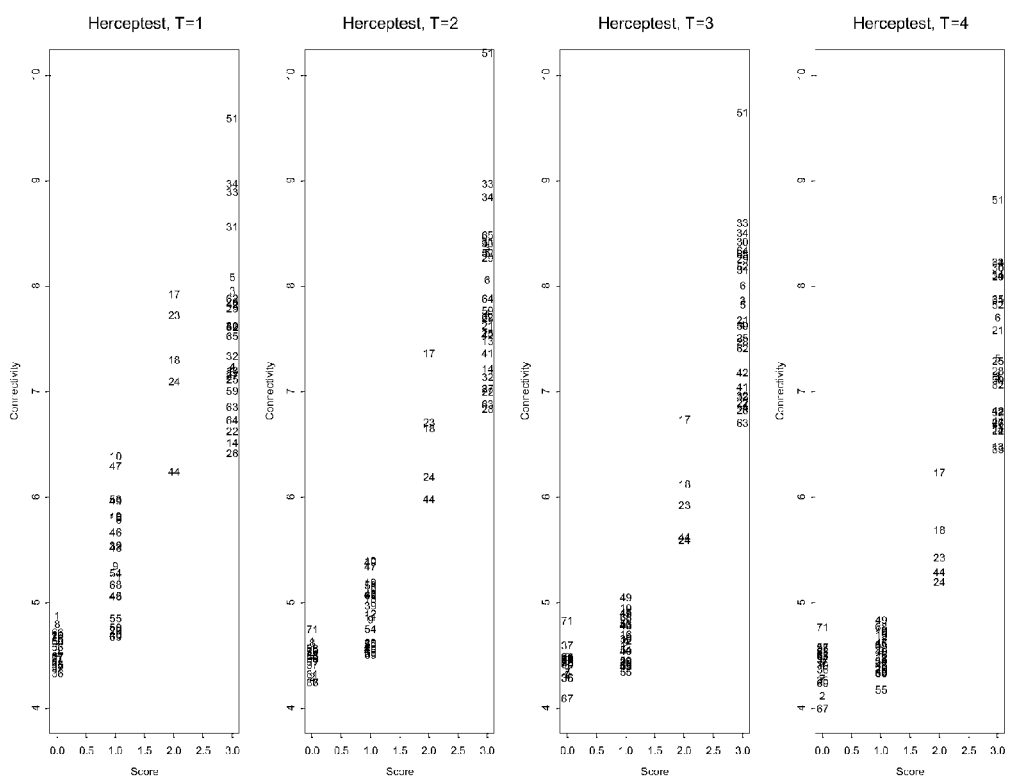
FIGS. 7a-7c show the results of an experimental series as detailed in Example 3 using the method of the present invention in the detection of breast cancer.
Figure 7B:
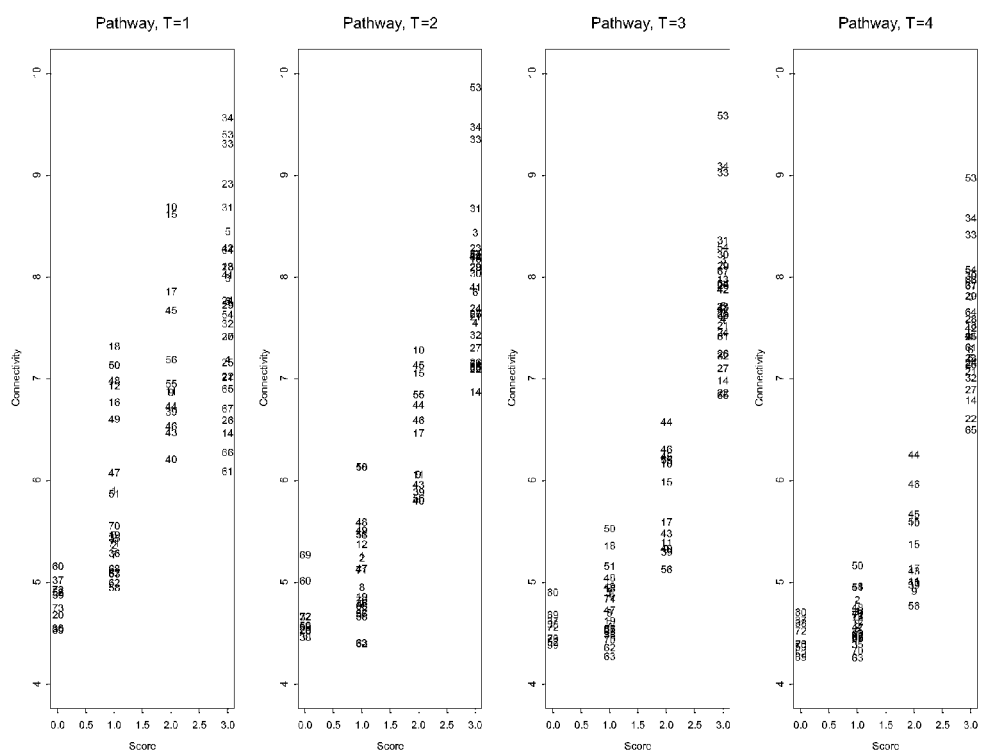

In FIG. 7a and FIG. 7b connectivity is plotted versus (manual) clinical score for each threshold level (T=1, 2, 3, and 4) for both Herceptest and Pathway.

The Membrane identification threshold that seems to work uniformly best for both reagents, in terms of connectivity, is the T=2 threshold.

A connectivity index around 5.6-5.7 seems ideal for separating 0 and +1 cases from the rest.

There are two obvious outliers for score=1 in the Pathway test. One appears to be an error in the manual scoring (should have been a +2), which is consistent with the fact that the same tumor specimen was scored 2 for the Herceptest, and the FISH amplification is ~1.5. The other outlier may be due to inclusion of in-situ areas in the analysis.

Figure 7C:
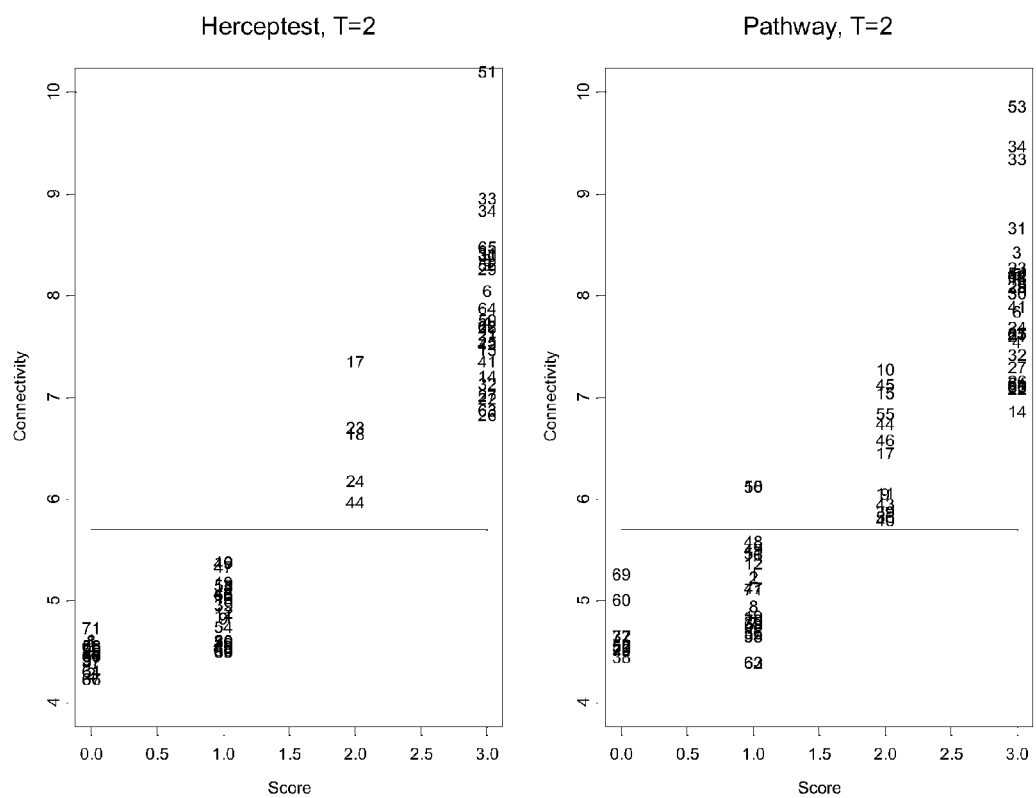

In FIG. 7c a comparison of the results for Herceptest and Pathway is seen. With the current measure of connectivity, the ideal cut-offs for both Herceptest and Pathway seems to be:
Negative (0 or +1) if Connectivity≤5.7
Positive (+2 or +3) otherwise.

Accordingly, by adding a measure of connectivity to the analysis the samples may be divided into groups corresponding to the manual grading.

Example 4

Diagnosing Breast Cancer Using a Determination of Red Chromaticity

On the same samples as used in Example 3, the Median Red Chromaticity (MRC) is plotted for the Herceptest and the Pathway data. This measure appears to be more robust than Average Red Chromaticity (ARC).

Figure 8A:
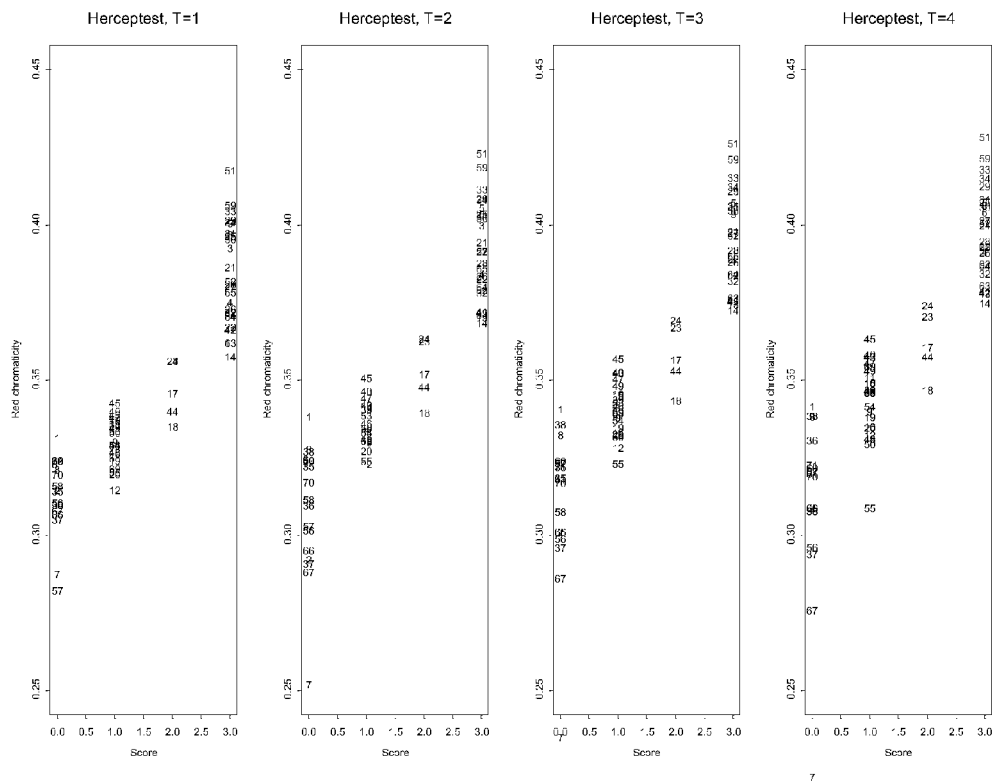
FIGS. 8a-8d show the results of an experimental series as detailed in Example 4 utilizing the present invention in the detection of breast cancer.
Figure 8B:
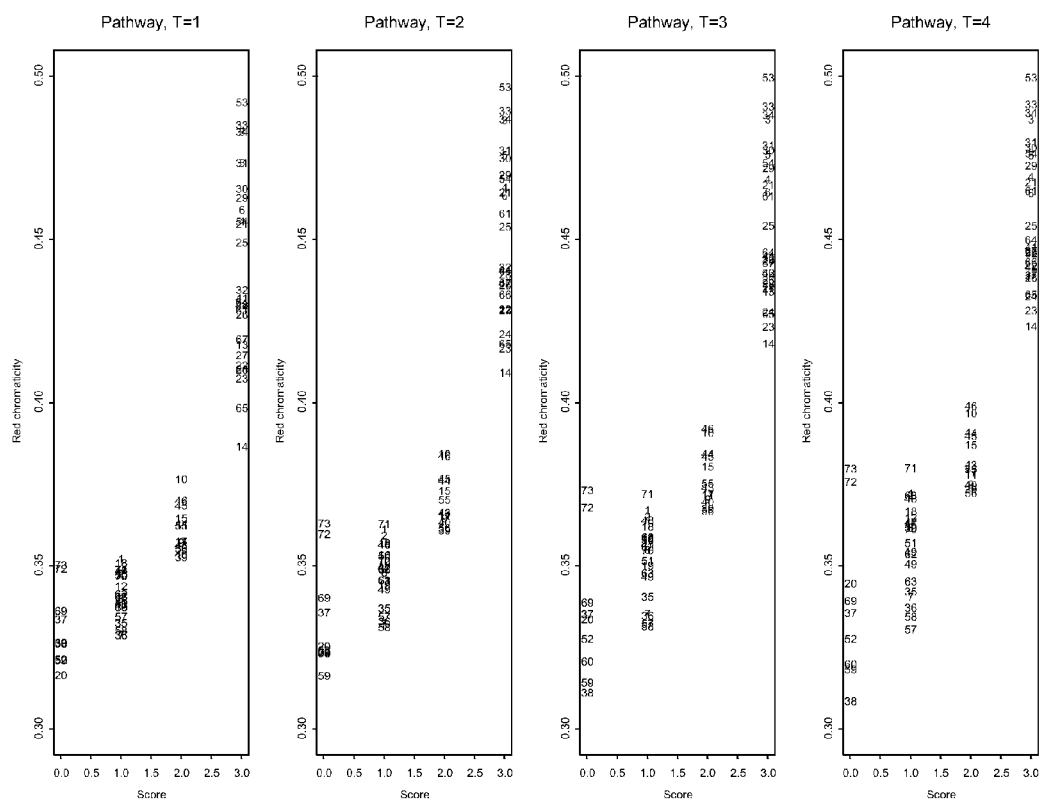

FIGS. 8a and 8b shows MRC is plotted versus (manual) clinical score for each threshold level (T=1, 2, 3, and 4) for both Herceptest and Pathway. It is noticed that chromaticity values for Pathway are generally higher than those observed for Herceptest, which is consistent with the empirical observation that Pathway specimens are generally darker than Hercerptest specimens.

It is also noticed that the overall ability for MRC to separate the different classes is better for Pathway than it is for Herceptest.

For Herceptest, the ability to discriminate between +1 and +2 is not particularly good. If however, the connectivity measure has been used for separating (0 and +1) from (+2 and +3), MRC appears well suited for discriminating within these two groups. For Pathway, it is not obvious that Connectivity contributes independent statistical information of use for discriminating between the diagnostic categories—for this dataset. There is, however, reason to suspect that the variability between different labs and batches would make the combination more robust in general.

Figure 8C:
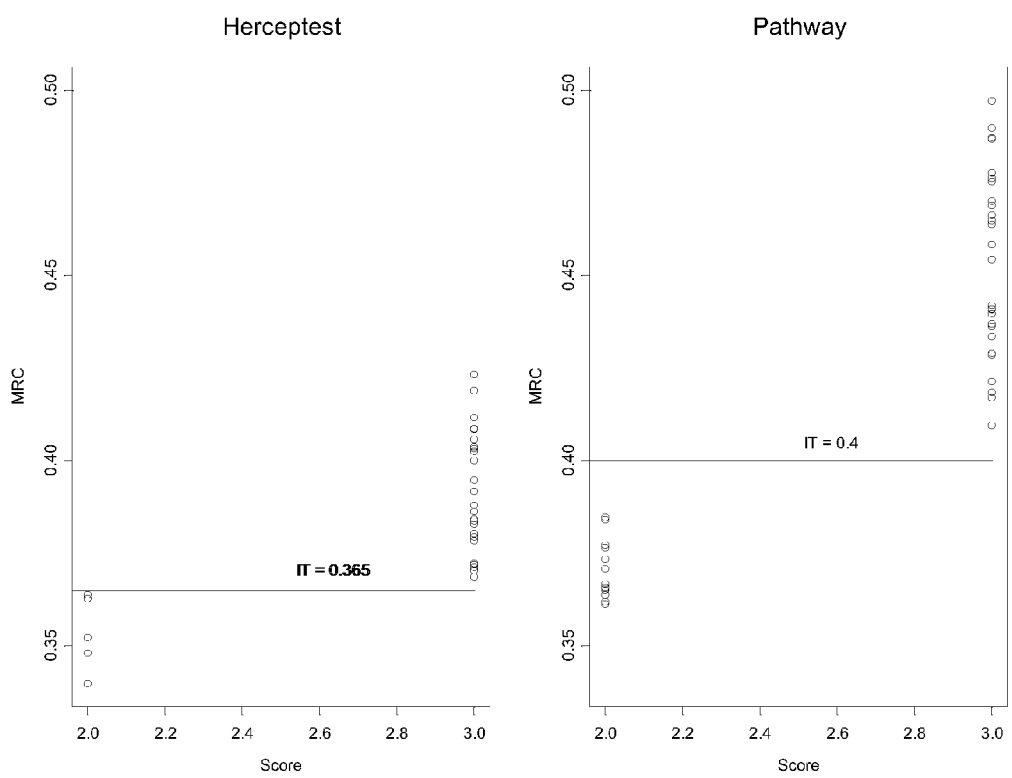
Figure 8D:
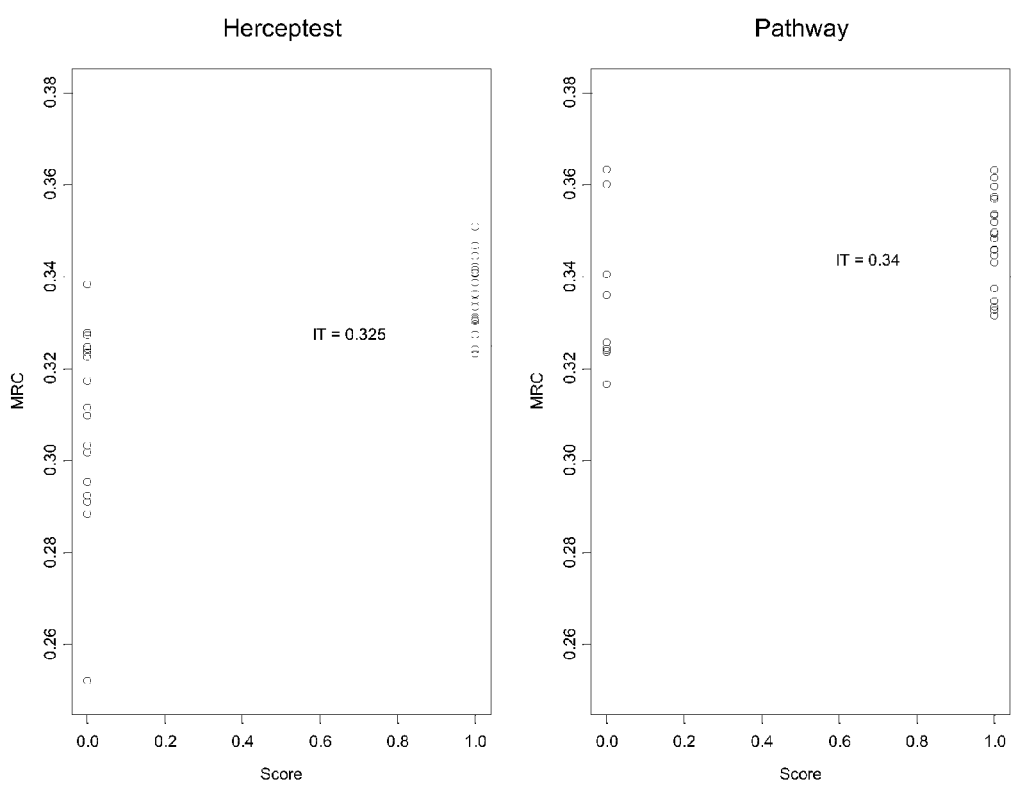

FIGS. 8c and 8d shows two separate cases: POSITIVE (+2, +3) or NEGATIVE (0, +1) which was previously determined by the connectivity index—both for Herceptest and Pathway.

FIG. 8c shows the POSITIVE cases. For Pathway the separation is very significant, based on the intensity feature (MRC). This is not the case for Herceptest, where the distinction becomes more "blurry". Again, this may be due to the fact that "irrelevant" objects are included in the analysis, which may ultimately be dealt with in a number of different ways.

Threshold for Herceptest and Pathway for POSITIVE cases, respectively:
Herceptest
+2 if MRC≤0.365
+3 otherwise.
Pathway
+2 if MRC≤0.4
+3 otherwise.

FIG. 8d shows the NEGATIVE cases. The distinction between 0 and +1 is somewhat blurry for both Herceptest and Pathway, although the difference in mean is significant. Again, this may be due to the fact that "irrelevant" objects are included in the analysis, which may ultimately be dealt with in a number of different ways.

Threshold for Herceptest and Pathway for NEGATIVE cases, respectively:
Herceptest
0 if MRC≤0.325
+1 otherwise.
Pathway
0 if MRC≤0.34
+1 otherwise.

Example 5

Diagnosing Breast Cancer Using Normalized Brown

On the samples as used in Example 3, the Median Normalized Brown (MBrown) is plotted for the Herceptest and the Pathway data. This measure appears to be more robust than Average Normalized Brown (ABrown).

Figure 9A:
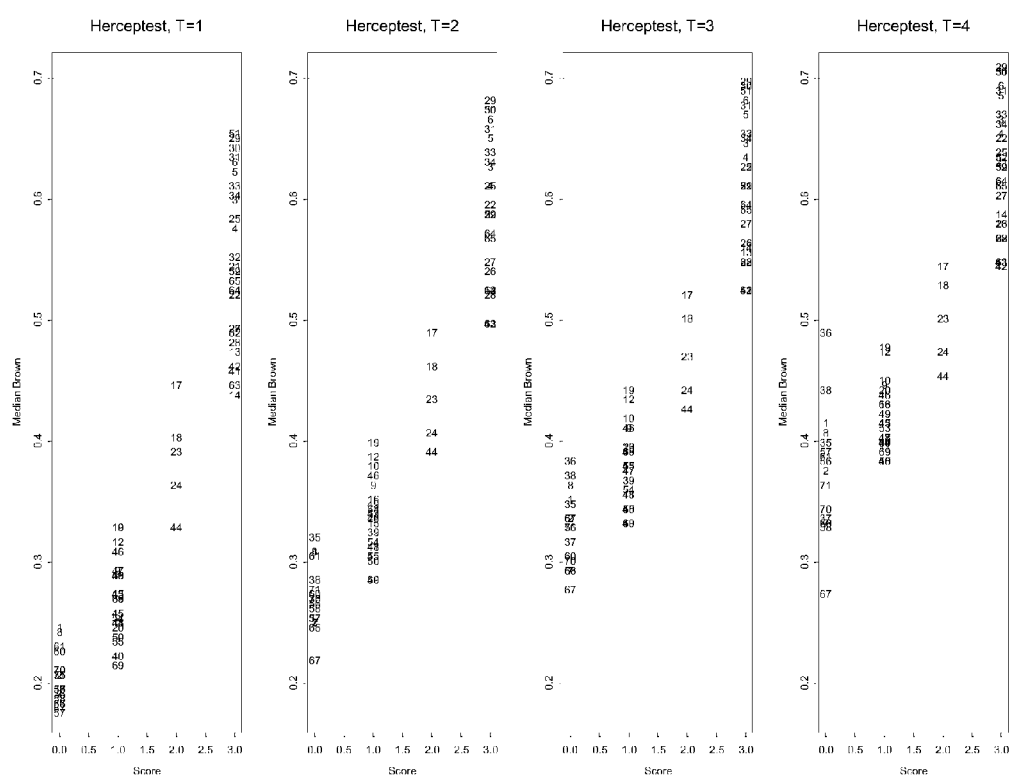
FIGS. 9a and 9b show the results of an experimental series as detailed in Example 5 using the present invention in the detection of breast cancer.
Figure 9B:
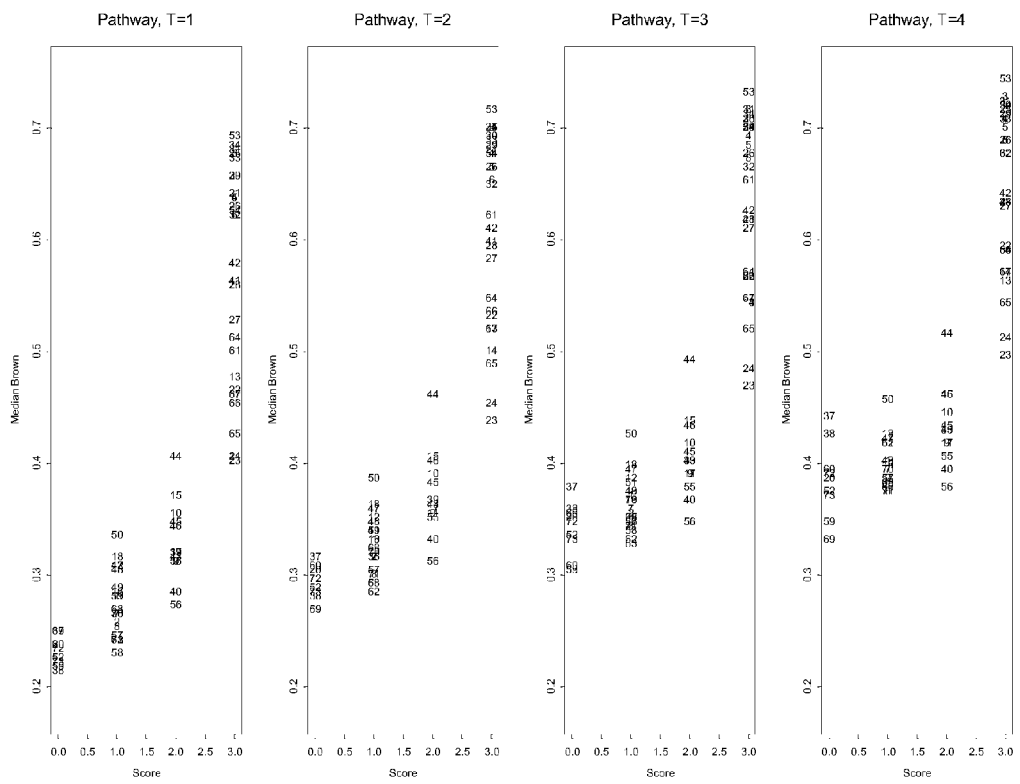

FIGS. 9a and 9b shows MBrown plotted versus (manual) clinical score for each threshold level (T=1, 2, 3, and 4) for both Herceptest and Pathway. It is clear that the MBrown feature is a better discriminator for diagnostic categories for the Herceptest than it is for the Pathway—i.e. the exact opposite situation as is seen for the MRC in Example 4.

Again, this feature appears to work uniformly best for the Membrane identification threshold corresponding to T=2.

The invention claimed is:

1. An automated system for identifying one or more stained targets in a biological sample comprising a slide scanner, and a view screen, and further, comprising, in combination:
  a database capable of including a plurality of digital representations of a plurality of biological samples, wherein said samples have been stained with a stain so as to define a stained target; and
  a software module for analyzing a plurality of pixels from at least one of said digital representations of said biological samples, and carrying out the following method for identifying one or more stained targets in said samples, said method comprising:
  a) providing at least one digital representation of the sample wherein the sample has been stained with a stain so as to define said stained target, and
  b) filtering the digital representation with at least three filters, each of said filters comprising filter constant(s), applying said filter constant(s) to each pixels in at least a subset of the digital representation and determining an eigensolution based on the filter output for each pixel in the subset, wherein said filters are capable of enhancing the stained targets obtaining a filtered representation,
  c) segmenting the digital representation based on information from the filtered representation into stained cell targets and background, thereby obtaining a segmented representation, wherein said segmented representation discriminates between stained targets and other structures in the digital representation, and;
  d) from said segmented representation, identifying the stained targets in the sample.

2. The system according to claim 1, wherein the filter constant(s) are estimated polynomial coefficients.

3. The system according to claim 2, wherein the polynomial coefficients are estimated from a second order polynomial, a fourth order polynomial, or a sixth order polynomial.

4. The system according to claim 1, wherein at least three filter constants are applied to the pixels in the subset.

5. The system according to claim 1, wherein the subset correspond to the entire digital representation.

6. The system according to claim 1, wherein the filter constant(s) is(are) determined prior to analysing a plurality of representations and the same constant(s) are used for each digital representation.

7. The system according to claim 1, wherein the filter constant(s) is(are) determined for each digital representation.

8. The system according to claim 2, wherein a Hessian matrix is determined for the polynomial coefficient, and the Eigensolution is determined from said Hessian matrix.

9. The system according to claim 2, wherein a least-squares estimator is used to determine the coefficient(s) of the polynomial.

10. The system according to claim 9, wherein the least-squares estimator is a weighted least-squares estimator.

11. The system according to claim 1, wherein the sample is a tissue sample.

12. The system according to claim 1, wherein the sample is a sample suspected of comprising cancer cells.

13. The system according claim 11, wherein the cancer cells are breast cancer cells.

14. The system of claim 1, wherein the stain is a chromophore or a fluorophore.

15. The system according to claim 1, wherein the stain stains for a target associated with the cell membrane.

16. The system according to claim 15, wherein the target is a protein associated with the cell membrane.

17. The system of claim 16, wherein the protein is selected from the HER-family, cytokeratins; and CD-antigens.

18. The system according to claim 1, wherein the stain stains for a target associated with linear structures outside the cell.

19. The system according to claim 18, wherein the target is a protein lining vessels or bronchi.

20. The system according to claim 1, wherein the Eigensolution is the first Eigen value.

21. The system according to claim 20, wherein the stain stains for at least one blob-shaped target in, on or outside the cell(s).

22. The system according to claim 1, wherein the Eigensolution is the second Eigen value.

23. The system according to claim 1, wherein the filtered representation is normalized with the intensity representation.

24. The system according to claim 1, wherein the segmented representation is post-processed.

25. The system according to claim 24, wherein the post-processing relates to elimination of stained cell membranes, extracellular linear structures or blobs having an area below or higher than a predefined area.

26. The system according to claim 1, wherein a measure for connectivity is computed as area of cell membranes divided with number of connected cell membranes.

27. The system according to claim 1, wherein the staining intensity in the segmented representation is calculated.

28. The system according to claim 27, wherein the staining intensity is calculated as the average staining intensity.

29. The system according to claim 28, wherein the staining intensity is calculated as the average staining intensity with respect to a red chromaticity value or a normalized brown value.

30. The system according to claim 2, wherein a window size for the polynomial is fitted to be larger than the size of the subset.

31. The system according to claim 1 suitable for classifying a sample, said system comprising in said control module instructions for carrying out a method of identifying one or more stained targets in said sample by a method as defined in claim 1, and based on the identified stained targets classifying the sample in relation to two or more groups of samples.

32. The system according to claim 31, wherein the classification is performed by statistically calculating the likelihood that the sample belongs to a specific group.

33. The system according to claim 31, wherein a quantification of stained targets are performed, and the classification is based on the quantification.

34. The system according to claim 1, wherein the slide scanner is a virtual slide scanner.

35. The system according to claim 1, wherein the filtered representation is normalized before the step of segmentation.

36. The system according to claim 1, wherein the filtered representation is combined with the digital representation.

37. The system according to claim 1, further comprising a slide loader, a barcode reader, a microscope and a stage.

* * * * *